US011911003B2

(12) United States Patent
McDowall et al.

(10) Patent No.: US 11,911,003 B2
(45) Date of Patent: Feb. 27, 2024

(54) SIMULTANEOUS WHITE LIGHT AND HYPERSPECTRAL LIGHT IMAGING SYSTEMS

(71) Applicant: Intuitive Surgical Operations, Inc., Sunnyvale, CA (US)

(72) Inventors: Ian E. McDowall, Woodside, CA (US); Jeffrey M. DiCarlo, Austin, TX (US); Brian D. Hoffman, Mountain View, CA (US); William Jason Culman, Santa Cruz, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1042 days.

(21) Appl. No.: 16/326,804

(22) PCT Filed: Sep. 8, 2017

(86) PCT No.: PCT/US2017/050758
§ 371 (c)(1),
(2) Date: Feb. 20, 2019

(87) PCT Pub. No.: WO2018/049215
PCT Pub. Date: Mar. 15, 2018

(65) Prior Publication Data
US 2019/0200848 A1 Jul. 4, 2019

Related U.S. Application Data

(60) Provisional application No. 62/385,700, filed on Sep. 9, 2016.

(51) Int. Cl.
*A61B 1/00* (2006.01)
*A61B 1/04* (2006.01)
(Continued)

(52) U.S. Cl.
CPC ........ *A61B 1/00193* (2013.01); *A61B 1/0005* (2013.01); *A61B 1/00186* (2013.01);
(Continued)

(58) Field of Classification Search
CPC .............. A61B 1/00193; A61B 1/0005; A61B 1/00186; A61B 1/04; A61B 1/042;
(Continued)

(56) References Cited

U.S. PATENT DOCUMENTS 8,169,468 B2  5/2012  Scott et al.
10,742,908 B2  8/2020  Pichette et al.
(Continued)

FOREIGN PATENT DOCUMENTS

CN   105263398 A   1/2016
JP   2006085688 A   3/2006
(Continued)

OTHER PUBLICATIONS

International Search Report and Written Opinion for Application No. PCT/US2017/050758, dated Dec. 14, 2017, 15 pages.
(Continued)

*Primary Examiner* — Sanjay Cattungal

(57) ABSTRACT

A computer-assisted surgical system simultaneously provides visible light and alternate modality images that identify tissue or increase the visual salience of features of clinical interest that a surgeon normally uses when performing a surgical intervention using the computer-assisted surgical system. Hyperspectral light from tissue of interest is used to safely and efficiently image that tissue even though the tissue may be obscured in the normal visible image of the surgical field. The combination of visible and hyperspectral images are analyzed to provide details and information concerning the tissue or other bodily function that were not previously available.

19 Claims, 11 Drawing Sheets

(51) Int. Cl.
*A61B 1/06* (2006.01)
*A61B 5/00* (2006.01)
*A61B 34/00* (2016.01)
*A61B 34/20* (2016.01)
*A61B 34/35* (2016.01)
*A61B 90/00* (2016.01)
*A61B 90/30* (2016.01)
*G02B 27/10* (2006.01)
*G06V 20/20* (2022.01)
*A61B 34/30* (2016.01)

(52) U.S. Cl.
CPC ............... *A61B 1/04* (2013.01); *A61B 1/042* (2013.01); *A61B 1/043* (2013.01); *A61B 1/0638* (2013.01); *A61B 5/0075* (2013.01); *A61B 34/00* (2016.02); *A61B 34/20* (2016.02); *A61B 34/35* (2016.02); *A61B 90/30* (2016.02); *A61B 90/361* (2016.02); *G02B 27/1006* (2013.01); *G06V 20/20* (2022.01); *A61B 2034/301* (2016.02); *A61B 2090/371* (2016.02); *G06V 2201/03* (2022.01)

(58) Field of Classification Search
CPC ..... A61B 1/043; A61B 1/0638; A61B 5/0075; A61B 34/00; A61B 34/20; A61B 34/35; A61B 90/30; A61B 90/361; A61B 2034/301; A61B 2090/371; A61B 34/70; A61B 90/37; G02B 27/1006; G02B 27/106; G06V 20/20; G06V 2201/03; G06V 40/10

See application file for complete search history.

(56) References Cited

U.S. PATENT DOCUMENTS

| | | | |
|---|---|---|---|
| 11,457,817 B2 * | 10/2022 | Sarvazyan | ........... A61B 5/0075 |
| 2002/0173723 A1 | 11/2002 | Lewis et al. | |
| 2007/0160279 A1 | 7/2007 | Demos | |
| 2008/0255457 A1 | 10/2008 | Khoobehi et al. | |
| 2012/0140981 A1 | 6/2012 | Berkman et al. | |
| 2012/0190981 A1 * | 7/2012 | Harris | ................... A61B 34/30 604/95.01 |
| 2013/0296709 A1 | 11/2013 | Zuzak et al. | |
| 2014/0085629 A1 | 3/2014 | Bodkin et al. | |
| 2014/0179997 A1 * | 6/2014 | von Grunberg | ... A61B 1/00183 600/102 |
| 2015/0042774 A1 | 2/2015 | Sugano et al. | |
| 2015/0250387 A1 * | 9/2015 | Hauger | ................ A61B 5/0071 600/476 |
| 2016/0015470 A1 | 1/2016 | Border | |
| 2016/0042513 A1 * | 2/2016 | Yudovsky | ............... G06T 7/337 382/128 |
| 2016/0086380 A1 * | 3/2016 | Vayser | ................... A61B 90/36 345/633 |
| 2016/0235482 A1 | 8/2016 | Wood et al. | |
| 2016/0248994 A1 * | 8/2016 | Liu | ...................... A61B 5/7445 |

FOREIGN PATENT DOCUMENTS

| | | |
|---|---|---|
| JP | 2011050470 A | 3/2011 |
| JP | 2011528918 A | 12/2011 |
| JP | 2012065698 A | 4/2012 |
| JP | 2015029841 A | 2/2015 |
| JP | 2015529482 A | 10/2015 |
| WO | WO-2005092008 A2 | 10/2005 |
| WO | WO-2015113460 A1 | 8/2015 |
| WO | WO-2015126466 A1 | 8/2015 |
| WO | WO-2016048911 A1 | 3/2016 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP17849646.9 dated May 4, 2020, 07 pages.

* cited by examiner

SIMULTANEOUS WHITE LIGHT AND HYPERSPECTRAL LIGHT IMAGING SYSTEMS

RELATED APPLICATIONS

This application claims priority to and the benefit of: U.S. Patent Application No. 62/385,700 (filed Sep. 9, 2016, disclosing "SIMULTANEOUS WHITE LIGHT AND HYPERSPECTRAL LIGHT IMAGING SYSTEMS," by Ian E. McDowall et al.)

BACKGROUND

Field of Invention

The present invention relates generally to imaging techniques used in surgical procedures, and more particularly to hyperspectral imaging combined with visual imaging.

Description of Related Art

Computer-assisted surgical system offers patients many benefits, such as reduced trauma to the body, faster recovery, and shorter hospital stay. One key component of the computer-assisted surgical system is a capability to provide two-channel (i.e., left and right) video capture and display of visible images to provide stereoscopic viewing for the surgeon.

Such electronic stereoscopic imaging systems may output high definition video images to the surgeon, and may allow features such as zoom to provide a "magnified" view that allows the surgeon to identify specific tissue types and characteristics, as well as to work with increased precision.

In a typical minimally invasive surgical field, certain tissue types are difficult to identify, or tissue of interest may be at least partially obscured by other tissue. This complicates the surgical procedure. In some applications, fluorescence images and reflected white light images are used in minimally invasive surgery. The fluorescence images assist in identifying tissue of interest.

There are various fluorescence imaging modalities. Fluorescence may result from the use of, for example, injectable dyes, fluorescent proteins, or fluorescent tagged antibodies. Fluorescence may result from, for example, excitation by laser or other energy source. Fluorescence images can provide vital in vivo patient information that is critical for surgery, such as pathology information (e.g., fluorescing tumors) or anatomic information (e.g., fluorescing tagged tendons).

Thus, visualization of tissue with fluorescence imaging is known in minimally invasive surgery. Further using near-infrared (NIR) light technology with indocyanine green (ICG; Akorn, Lake Forest, IL, USA) as the fluorescent agent has been used in minimally invasive surgery with the da Vinci Si Surgical System.

For example, Hellen et al., "The influence of fluorescence imaging on the location of bowel transection during robotic left-sided colorectal surgery." Surg. Endosc., 3 Jan. 2014, DOI 10.1007/s00464-013-3377-6, describe systematically evaluating the impact of fluorescence imaging on the location of colonic and rectal transection lines based on evaluation of perfusion with indocyanine green (ICG) and near infrared light technology.

It also is known, for example, to use fluorescence in locating ureters. An IV injection or a catheter-based retrograde injection of a near infrared (NIR) fluorophore was used to image the ureters using infrared illumination. It was reported that the ureters could be visualized even when embedded in surrounding tissue, and injury could be assessed in real time using invisible light. Eiichi Tanaka, et al. "Real-Time Intraoperative Ureteral Guidance Using Near-Infrared Fluorescence," J. Urol. 178(5), pgs. 2197-2201 (2007) describe using Indocyanine green (ICG) and CW800-CA, the carboxylic acid form of IRDye™ 800CW NIR dye, from LI-COR (Lincoln, NE) as the NIR fluorophores. Aya Matsui, M. D., et al., "Real-Time Near-Infrared Fluorescence-Guided Identification of the Ureters using Methylene Blue," Surgery, 148(1) pgs. 78-86 (2010) use methylene blue as the NIR fluorophore.

Another approach to locate the ureters used infrared thermography. Room-temperature saline was used as an irrigant in the operative field so that the whole operative field was cooled temporarily. As the operative field differentially rewarmed, structures such as blood vessels rewarmed quickly and appeared as white lines against a dark background in an infrared image. A second application of this same concept involved filling the upper urinary system with room-temperature saline. The pelvis and ureter appeared black against a warmer background, which appeared white in an infrared image. See Jeffrey A. Cadeddu, M. D., et al, "Laparoscopic Infrared Imaging," Journal of Endourology, Vol. 15, No. 1, pgs. 111-116(2001).

SUMMARY

A surgical system includes an illuminator and a camera. The illuminator includes a white light illumination source and a hyperspectral illumination source. The camera includes a sensor assembly. The sensor assembly includes a first image capture sensor and a second image capture sensor. The first image capture sensor is configured to capture a visible color frame and the second image capture sensor is configured to capture a hyperspectral frame. The first and second image capture sensors capture the visible color frame and the hyperspectral frame substantially simultaneously.

In one aspect, the camera is mounted on the robotic arm of the surgical system. A controller of the surgical system is coupled to the illuminator and is coupled to the camera. The controller is configured to command the robotic arm to move the camera to each of a plurality of locations, and the controller is configured to command the camera to simultaneously capture at each of the plurality of locations a visible color frame and a hyperspectral frame.

In another aspect, the controller is configured to command the illuminator to output a time sequence of hyperspectral wavebands. In this aspect, the controller is configured to command the camera to substantially simultaneously capture, for each of the plurality of hyperspectral wavebands, a visible color frame and a hyperspectral frame.

In yet another aspect, the controller is configured to command the camera to capture a set of hyperspectral frames and to capture a visible frame. The controller is configured to generate a composite frame from the set of hyperspectral frames. The visible frame includes a visible scene of a surgical site, and the composite frame includes a feature of the surgical site that is visibly salient in the visible scene.

The surgical system also includes a display unit coupled to the controller to receive the composite frame and the visible frame. The frames are processed to identify feature(s) (or enhance the visibility of features) and the display unit displays the feature(s) superimposed with the visible scene.

In another aspect the display unit is configured to displaying the feature superimposed with the visible scene in a picture within a picture.

The camera includes a lens assembly common to the first image capture sensor and the second image capture sensor. The camera also includes a beam splitter positioned between the lens assembly and the first and second image capture sensors. In one aspect, the camera includes a filter assembly positioned between the beam splitter and the second image capture sensor.

The filter assembly is positioned to filter light focused on the second image capture sensor. In one aspect, the filter assembly is a striped filter. In another aspect, the filter assembly is a filter linearly variable with wavelength in one dimension.

In one aspect, an endoscope includes the illuminator and the camera. In another aspect, an endoscope is mounted on a first manipulator. The endoscope includes the camera. A surgical device is mounted on a second manipulator. The surgical device includes the illuminator.

In still another aspect, a surgical system includes a controller configured to receive a sequence of visible color frames and a sequence of hyperspectral frames. The controller is configured to create a composite hyperspectral frame from a set of hyperspectral frames in the sequence of hyperspectral frames corresponding to each of the visible color frames in the sequence of color frames. A display unit is coupled to controller to receive the sequence of visible frames and the composite frame for each of the visible frames.

In one aspect, the display unit is configured to display the sequence of visible frames, and is configured to display a picture-in-a-picture in the display of the sequence of visible frames, the picture-in-a-picture being a sequence of each of the visible frames superimposed with the corresponding composite frame.

In a further aspect, a surgical system includes a first surgical device and a second surgical device. The first surgical device includes a first image capture unit configured to capture a visible color frame. The second surgical device includes a second image capture unit configured to capture a hyperspectral frame. The first and second image capture units capture the visible color frame and the hyperspectral frame substantially simultaneously and provide the images to an image processing unit.

In one aspect, the second surgical device includes a depth sensing unit. In another aspect, the second surgical device is a cannula.

DETAILED DESCRIPTION

Aspects of this invention augment a video capturing and video viewing capability of surgical devices, e.g., computer-assisted surgical systems such as the da Vinci® Surgical System commercialized by Intuitive Surgical, Inc. of Sunnyvale, California, by incorporating both visible images and alternate modality images to identify tissue or other aspects of clinical interest during surgery. (da Vinci® is a registered trademark of Intuitive Surgical, Inc. of Sunnyvale, California) While a computer-assisted surgical system is used herein as an example, aspects of this invention can be used with any device or system that displays an image of a surgical field to assist the surgeon during a surgical procedure.

Aspects of the invention simultaneously provide alternate modality images that identify tissue or other features of clinical interest in addition to the visible images that a surgeon normally uses when performing a surgical operation using a computer-assisted surgical system. In one aspect, hyperspectral light from tissue of interest is used to safely and efficiently image that tissue even though the tissue may be obscured in the normal visible image of the surgical field. In another aspect, the combination of visible and hyperspectral imaging is analyzed to provide details and information concerning the tissue or other bodily function that were not previously available. Herein, hyperspectral light refers to spectral information in light that does not relate to a feature that is visible by a human.

This imaging combination may be an overlay of the visible and alternate images, the overlay of alternate images may be toggled on and off (e.g., by using a foot pedal or by double-clicking master finger grips on the da Vinci® Surgical System surgeon's console). In one aspect, the superposition of the visible and alternate images—the combination picture—is presented as a picture within a picture, where the combination picture is presented as a picture within the normally displayed scenes of a surgical site viewed by the surgeon, or alternatively, the normally displayed scenes of the surgical site are presented as a picture within the combination picture. In one aspect, the scene in the combination picture trails in time the scene normally displayed to the surgeon due to the processing required to generate the combination picture.

Figure 1:
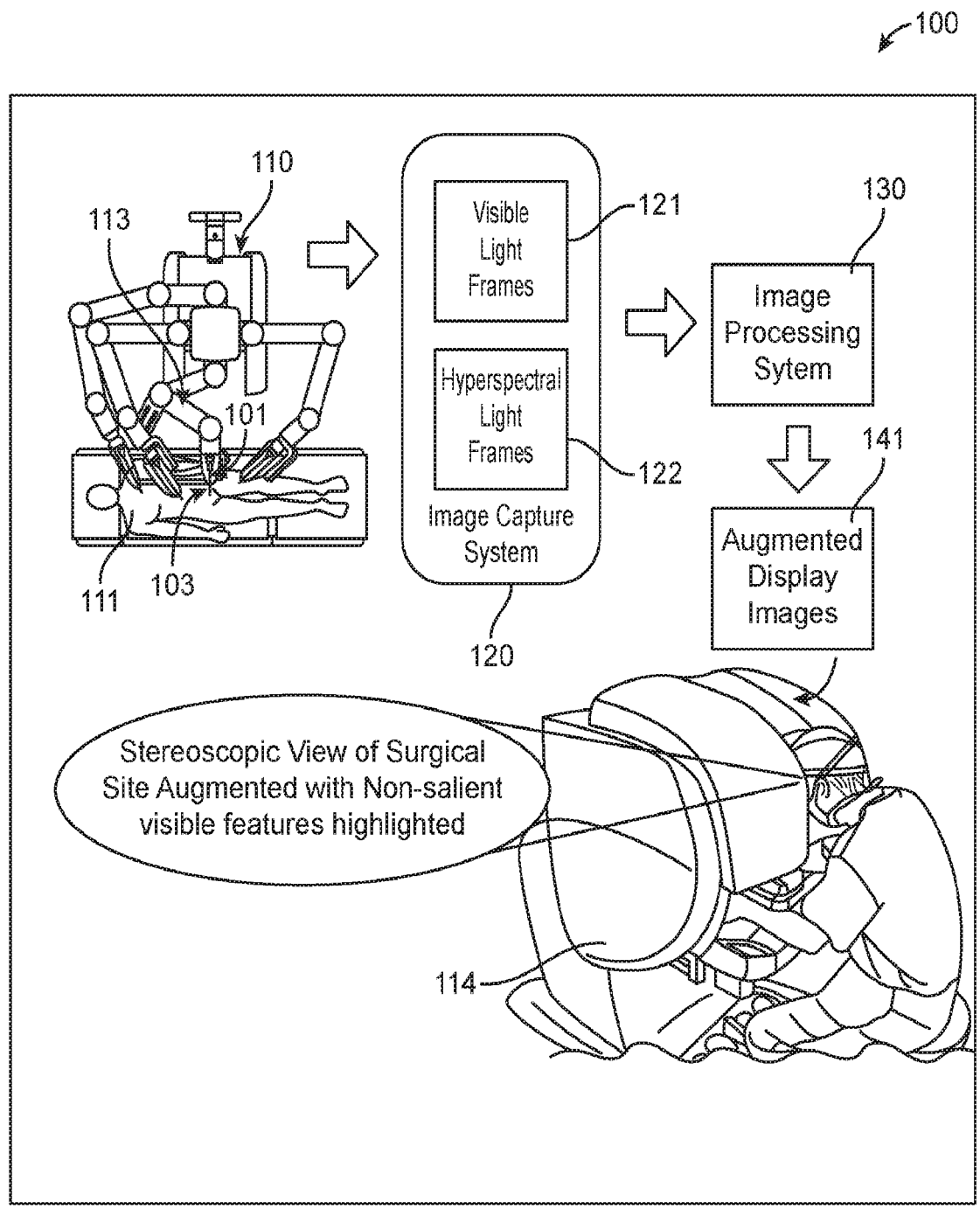
FIG. 1 is a high level diagrammatic view of a computer-assisted surgical system, which includes a simultaneous visual and hyperspectral imaging capability.

FIG. 1 is a high level diagrammatic view of a computer-assisted surgical system 100, for example, the da Vinci® Surgical System. In this example, a surgeon, using a surgeon's console 114, remotely manipulates an endoscope 101 using a robotic manipulator arm 113. The surgeon can also manipulate surgical instruments mounted on other robotic manipulator arms. There are other parts, cables etc. associated with computer-assisted surgical system 100, but these are not illustrated in FIG. 1 to avoid detracting from the disclosure. Further information regarding computer-assisted surgical systems may be found, for example, in U.S. Patent Application Publication No. US 2008-0065105 A1 (filed Jun. 13, 2007; disclosing Minimally Invasive Surgical System) and U.S. Pat. No. 6,331,181 (filed Dec. 18, 2001; disclosing Surgical Robotic Tools, Data Architecture, and Use), both of which are incorporated herein by reference.

As explained more completely below, an illumination system (not shown) is coupled to or alternatively included within endoscope 101. In one aspect, the illumination system provides white light illumination or a combination of white light illumination and hyperspectral light illumination. In one aspect, all or part of this light is coupled to at least one illumination path in endoscope 101. In another aspect, the illumination sources are located at or near the distal tip, or in the backend housing, of endoscope 101. In one aspect, both the visible white light illumination and the hyperspectral illumination are constant during the surgical procedure. In another aspect, the visible illumination is constant in time, but the spectrum of the hyperspectral illumination changes with time.

In this aspect, light from endoscope 101 illuminates tissue 103 of a patient 111. Endoscope 101, in one aspect, is a stereoscopic endoscope, which includes two optical channels, e.g., a left optical channel and a right optical channel, for passing light from the tissue, e.g., reflected white light and reflected or emitted hyperspectral light. Endoscope 101, in another aspect, is a monoscopic endoscope, which includes a single optical channel for passing light from the tissue, e.g., reflected white light and reflected or emitted hyperspectral light.

As explained more completely below, for both types of endoscopes, the reflected white light is captured as visible light frames 121 by an image capture system 120. Visible light frames 121 include visible scenes that include images of tissue 103, and visible light frames 121 sometimes are referred to as visible frames 121.

Reflected and/or emitted hyperspectral light is captured as hyperspectral light frames 122 by image capture system 120. Hyperspectral light frames 122 include hyperspectral scenes of tissue 103 or other features in the field of view of endoscope 101. Hyperspectral light frames 122 sometimes are referred to as hyperspectral frames 122. Image capture unit 120 captures a visible frame and a hyperspectral frame substantially simultaneously. Here, substantially simultaneously, effectively simultaneously, nearly simultaneously, and substantially concurrently capture of a visible frame and a hyper spectral frame mean that from a human perspective the two frames appear to be captured at a same point in time.

In one aspect, cameras in image capture system 120 are mounted on a proximal end of endoscope 101. In another aspect, the cameras are mounted in a distal end of endoscope 101. Here, distal means closer to the surgical site and proximal means further from the surgical site. As explained more completely below, the cameras capture the visible and hyperspectral frames through the same front end optics, in one aspect. This is contrast to systems that utilize special front end optics to capture hyperspectral frames.

In one aspect, at predetermined time intervals, a stereoscopic pair of hyperspectral frames 122 is captured substantially simultaneously with a corresponding pair of stereoscopic visible frames 121. Thus, image capture system 120 enables capture of a frame 121 with a white light scene, e.g., a visible color scene, and also enables capture of information that is not salient in the visible color scene, i.e., capture of a hyperspectral frame 122. Typically, captured hyperspectral frames 122 do not necessarily have the same resolution as captured visible frames 121, because the resolution of the sensor used to capture hyperspectral frames 122 may in some cases be less than the resolution of the sensor used to capture visible frames 121. The technology used to implement the image sensors for the visible and the hyperspectral images may differ based on the implementation details for best sensitivity, noise reduction, and imaging performance in the required wavelength ranges needed for the imaging.

Consequently, a set of one or more hyperspectral frames is captured, and this set of hyperspectral frames is spatially registered to a corresponding captured visible frame. Spatially registered means the spatial points in each of the hyperspectral frames are mapped so that common spatial points in each of the captured hyperspectral frames can be aligned so that the set of hyperspectral frames can be superimposed or approximately superimposed to form a composite hyperspectral frame, and that spatial points of the composite hyperspectral frames are mapped to corresponding spatial points in the visible frame so that the composite hyperspectral frame and the visible frame can be superimposed to form a combination frame, which is sometimes referred to an augmented scene.

The tissue at a surgical site is typically moving due to, for example, any one of or any combination of breathing, beating of the heart, other body motion or peristalsis, and/or blood flow. This movement makes spatial registration more difficult, but in a computer-assisted surgical system, the pose (the position coordinates and orientation coordinates) of the camera is known for each image captured and can be used in the spatial registration process.

In one aspect, image processing system 130 creates an augmented scene 141, i.e., the visible scene in the visible frame is superimposed with the composite scene formed by superimposition of the set of hyperspectral frames. In some aspects, the combination of the visible and hyperspectral data is transformed for presentation to the surgeon, e.g., the data is processed to identify specific features of interest. Augmented scene 141 is displayed in the stereoscopic viewer of surgeon's console 114. Since the set of hyperspectral frames captures features that are not salient in the visible scene, e.g., features that are not visible or not clearly visible in the scenes of the visible frames, the augmented image provides more information to the surgeon than is available in the visible scene, e.g., the location of tissue of interest, such as diseased tissue, nerves, ureters, etc.

In another aspect, the stereoscopic viewer of surgeon's console 114 has a picture in a picture capability. When the user of system 100 selects the picture in a picture view mode, the normal view of the surgical site is presented and the picture within the picture presents the surgeon with another view of the surgical site with non-salient features highlighted. Alternatively, in the picture in a picture view mode, the surgeon is presented with the view of the surgical site with non-salient features highlighted and the picture in a picture presented the normal view of the surgical site. In both cases, the same visible surgical site scene is presented in both pictures, but in the augmented scene, the visible surgical site scene may trail in time the same surgical site scene in the normal view.

Also, when depth information is available, e.g., from frames captured by a stereoscopic camera or from an endoscope that includes a depth sensing device, the information in the hyperspectral frames can be analyzed to determine the absolute reflectance, as compared with the relative reflectance, of tissue. The absolute reflectance permits, for example, the determination of diseased tissue, or the clinical assessment of the rate of hepatic function in absolute terms.

Figure 2:
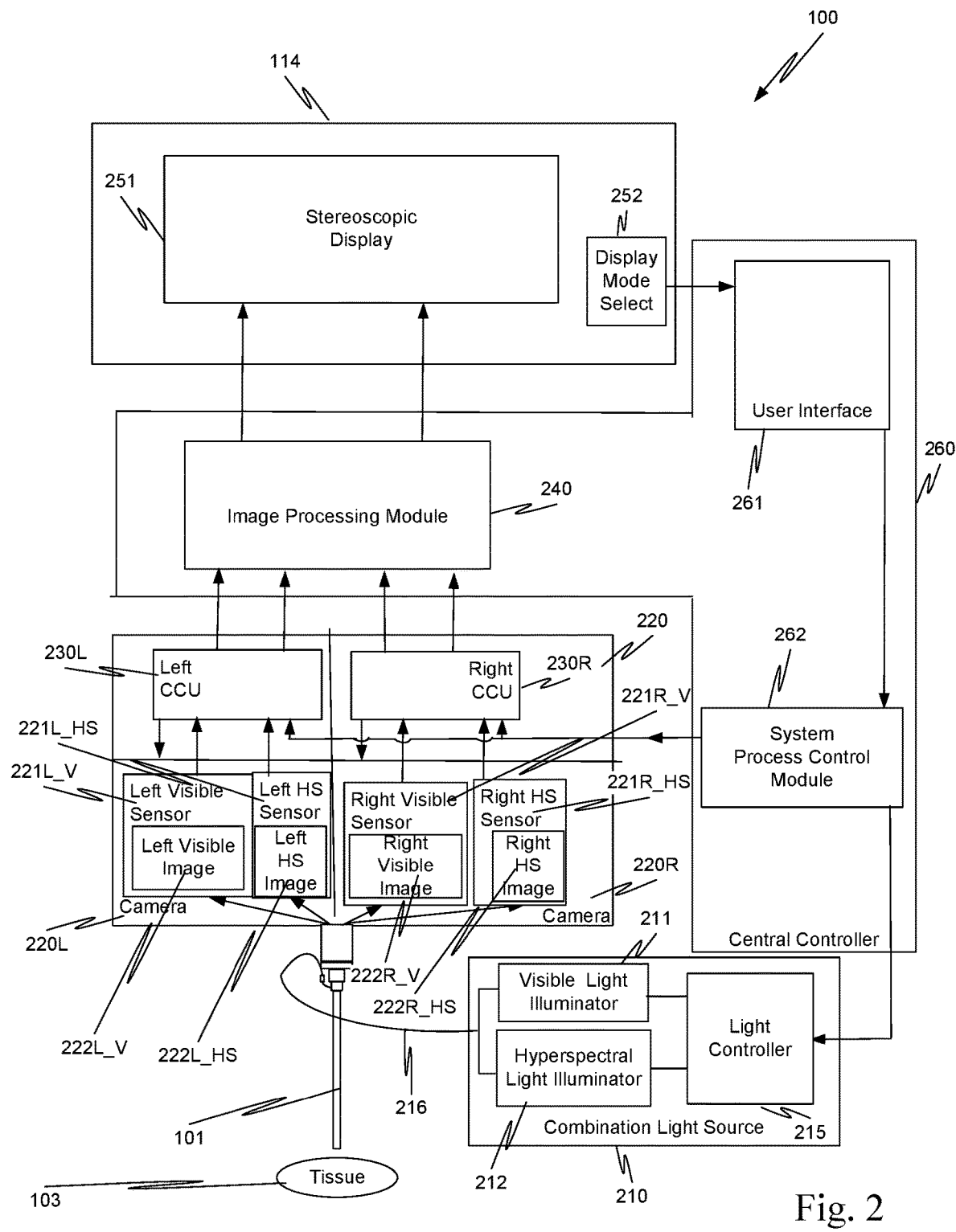
FIG. 2 is a more detailed illustration of the aspects of one example of the computer-assisted surgical system 100 of FIG. 1.
Figure 3:
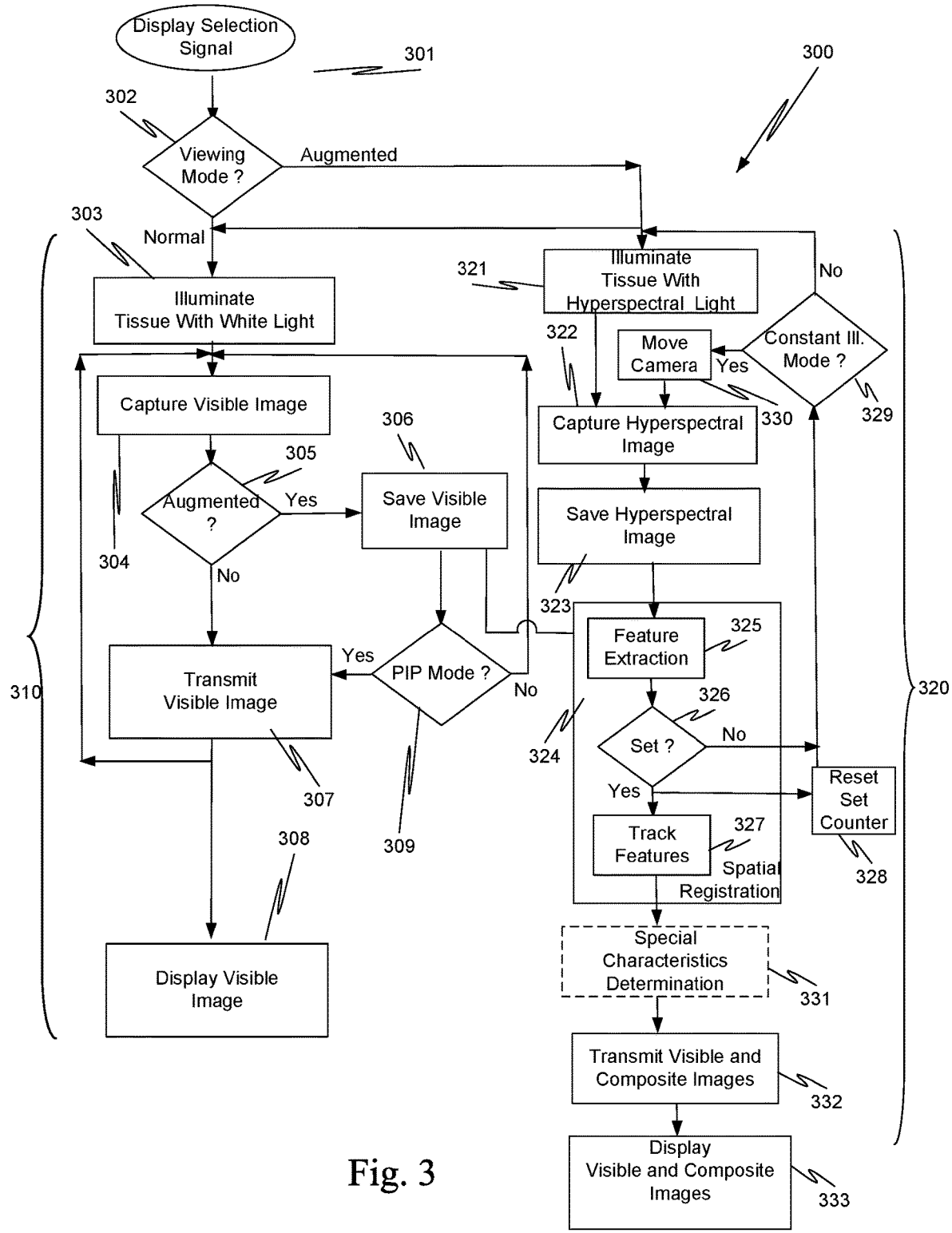
FIG. 3 is a process flow diagram for the operation of the system in FIG. 2.
Figure 4:
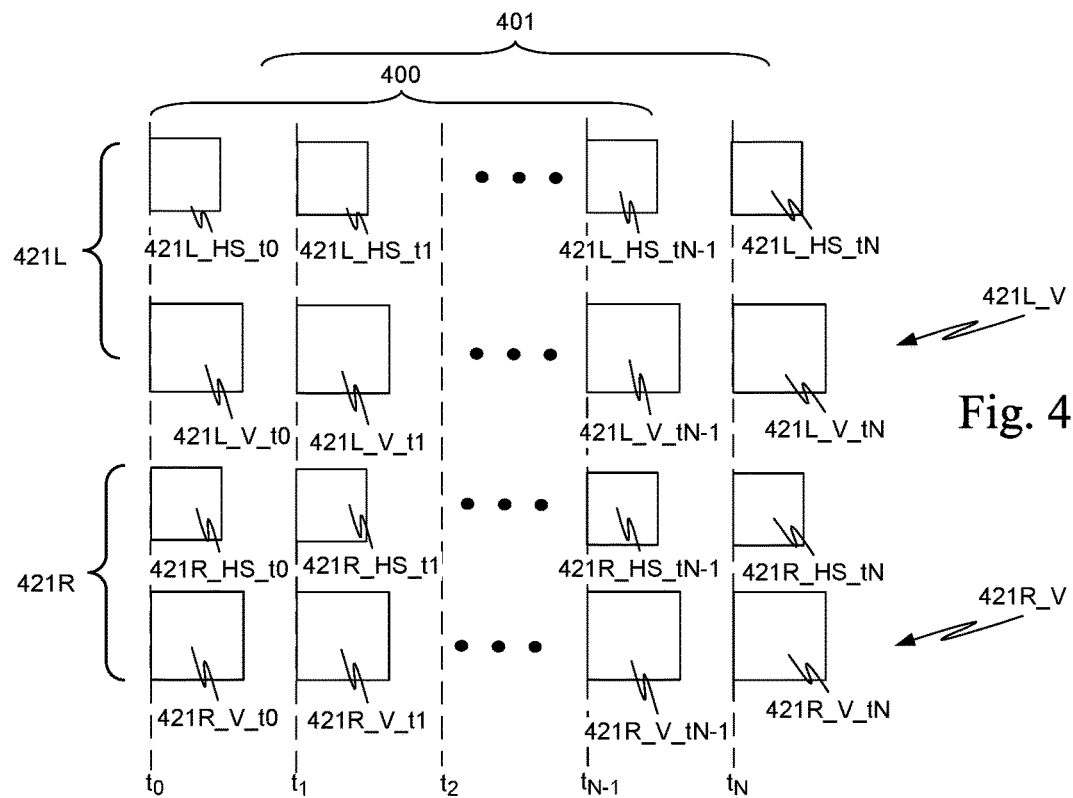
FIG. 4 is a timing diagram for the illumination of tissue and the capture of images in the system of FIG. 2.

FIG. 2 is a more detailed illustration of the aspects of one example of computer-assisted surgical system 100 of FIG. 1. FIG. 3 is a process flow diagram for the operation of the system in FIG. 2, while FIG. 4 is a timing diagram for the illumination of tissue and the capture of images in the system of FIG. 2. The timing diagram applies to both constant hyperspectral illumination and time sequential hyperspectral illumination.

In the embodiment of FIG. 2, computer assisted surgical system 100 includes an illuminator that is a combination light source 210. Combination light source 210 includes a visible light illuminator 211, e.g., a white light source, and a hyperspectral light illuminator 212. The particular implementation of illuminators 211 and 212 is not critical so long as combination light source 210 has the capabilities described more completely below.

In this aspect, combination light source 210 is used in conjunction with at least one illumination path in a stereoscopic endoscope 101 to illuminate tissue 103. In one aspect, combination light source 210 has at least two modes of operation: a normal viewing mode and an augmented viewing mode. In one aspect, the augmented viewing mode is broken into a constant hyperspectral illumination mode and a time sequential hyperspectral illumination mode.

In the normal viewing mode, visible light illuminator 211 provides illumination that illuminates tissue 103 in white light. Hyperspectral light illuminator 212 is not used in the normal viewing mode.

In the augmented viewing mode, visible light illuminator 211 provides illumination that illuminates tissue 103 in white light. In one aspect, hyperspectral light illuminator 212 provides illumination that illuminates tissue 103 with a constant in time spectrum of hyperspectral light, e.g., light in the infrared spectrum. In another aspect, hyperspectral light illuminator 212 provides illumination that illuminates tissue 103 with time sequential wavebands of hyperspectral light, e.g., wavebands of light in the infrared spectrum.

Use of infrared or near-infrared light as an example of hyperspectral illumination is illustrative only and is not intended to be limiting to this particular aspect. In view of the disclosure, one knowledgeable in the field can select hyperspectral illumination that makes the non-salient features in the captured visible frames salient in the captured hyperspectral frames.

In one aspect, visible light illuminator 211 includes a source for each of the different visible color illumination components. For a red-green-blue implementation, in one example, the sources are lasers, a red laser, two green lasers and a blue laser.

The use of lasers in visible light illuminator 211 is illustrative only and is not intended to be limiting. Visible light illuminator 211 could also be implemented with multiple LED sources instead of lasers for example. Alternatively, visible light illuminator 211 could use a Xenon lamp with an elliptic back reflector and a band pass filter coating to create broadband white illumination light for visible images. The use of a Xenon lamp also is illustrative only and is not intended to be limiting. For example, a high pressure mercury arc lamp, other arc lamps, or other broadband light sources may be used.

The implementation of hyperspectral light illuminator 212 depends on the hyperspectral spectrum of interest Typically, a laser module, laser modules, a light-emitting diode or light emitting diodes are used as hyperspectral light illuminator 212. If hyperspectral light illuminator 212 provides a time constant spectrum of hyperspectral light, a rotating filter can be used to filter the output of hyperspectral light illuminator 212, and so generate time sequential wavebands of hyperspectral light. A linearly variable filter may also be used and slid across the light path. Two such filters may also be used to selectively produce a band of illumination. Filters used in this way may also be patterned in such a way that when moved relative to each other, the desired spectral illuminant is created.

In the normal and the augmented viewing modes, the light from visible light illuminator 211 or light from visible light illuminator 211 and light from hyperspectral light illuminator 212 is directed into a connector 216. Connector 216 provides the light to an illumination path in stereoscopic endoscope 101 that in turn directs the light to tissue 103. Each of connector 216 and the illumination path in stereoscopic endoscope 101 can be implemented, for example, with a fiber optic bundle, a single stiff or flexible rod, or an optical fiber.

Light from surgical site 103 (FIG. 2) is passed by the stereoscopic optical channel in endoscope 101, e.g., a left optical channel and a right optical channel, or alternatively, a first optical channel and a second optical channel, to cameras 220L, 220R. As explained more completely below, left camera 220L includes a left visible color image capture sensor 221L_V and a left hyperspectral image capture sensor 221L_HS. Left visible color image capture sensor 221L_V captures visible light received from the left channel of stereoscopic endoscope 101 as a left visible frame 222L_V. Left hyperspectral image capture sensor 221L_HS captures hyperspectral light, or hyperspectral and visible light received from the left channel of stereoscopic endoscope 101 as a left hyperspectral frame 222L_HS.

Similarly, right camera 220R includes a right visible color image capture sensor 221R_V and a right hyperspectral image capture sensor 221R_HS. Right visible color image capture sensor 221R_V captures visible light received from the right channel of stereoscopic endoscope 101 as a right visible frame 222R_V. Right hyperspectral image capture sensor 221R_HS captures hyperspectral light, or hyperspectral and visible light received from the right channel of stereoscopic endoscope 101 as a right hyperspectral frame 222R_HS.

Both left camera 220L and right camera 220R capture a visible frame and a hyperspectral frame substantially simultaneously. The captured visible frame and the captured hyperspectral frame are captured through the same front end optics. This is in contrast to prior hyperspectral image capture systems that use specialized front end optics to capture hyperspectral images.

Typically, but not necessarily, the resolution of the hyperspectral image capture sensors is less than the resolution of the visible color image capture sensors. For example, the pixels in the visible color image capture sensors have a size ranging from 1.2 to 2.2 micro-meters, while the pixels in the hyperspectral image capture sensors have as size in the range of 2 to 10 micro-meters. Thus, to obtain a useful hyperspectral image, as explained more completely below, a plurality of hyperspectral frames are used to generate a composite hyperspectral frame for a point in time. The composite hyperspectral frame includes information that typically is not salient in the captured visible frame.

Camera 220L is coupled to a stereoscopic display 251 in surgeon's console 114 by a left camera control unit 230L and image processing module 240. Image processing module 240 is a part of image processing system 130. Camera 220R is coupled to stereoscopic display 251 in surgeon's console 114 by a right camera control unit 230R and image processing module 240. Camera control units 230L, 230R receive signals from a system process control module 262. System process control module 262 represents the various controllers in system 100.

Display mode select switch 252 provides a signal to a user interface 261 that in turn passes the selected display mode to system process control module 262. Various controllers within system process control module 262 configure illumination controller 215, configure left and right camera control units 230L and 230R to acquire the desired images, and configure any other elements in imaging processing module 240 needed to process the acquired scenes so that the surgeon is presented the requested scenes in stereoscopic display 251. Imaging processing modules 240 implement image processing pipelines equivalent to known image processing pipelines, except for the details provided herein.

The video output on stereoscopic display 251 may be toggled between the normal and augmented viewing modes by using, e.g., a foot switch, a double click of the master grips that are used to control the surgical instruments, voice control, and other like switching methods. The toggle for switching between the viewing modes is represented in FIG. 2 as display mode select 252.

Central controller 260 and system process control module 262 are similar to prior systems with the exception of the aspects described more completely below. Although described as a central controller 260, it is to be appreciated that controller 260 may be implemented in practice by any number of modules and each module may include any combination of components. Each module and each component may include hardware, software that is executed on a processor, and firmware, or any combination of the three.

Also, the functions and acts of controller 260 and system process control module 262, as described herein, may be performed by one module, or divided up among different modules or even among different components of a module. When divided up among different modules or components, the modules or components may be centralized in one location or distributed across system 100 for distributed processing purposes. Thus, central controller 260 and system process control module 262 should not be interpreted as requiring a single physical entity as in some aspects both are distributed across system 100.

Herein, the capture, processing, and display of images captured by camera 220L is the same as the capture, processing, and display of images captured by camera 220R. Thus, in the following description, when only frames captured from light in one channel of a stereoscopic endoscope are discussed that discussion is also directly applicable to the frames captured from light in the other channel of the stereoscopic endoscope. Thus, the description is not repeated for the other channel of the stereoscopic endoscope.

Moreover, in a monoscopic endoscope, only frames equivalent to the frames captured, for example, by camera 220L are available. Thus, the aspects described herein that do not require a stereoscopic image are also directly applicable to a monoscopic endoscope.

Further information regarding computer-assisted surgical systems may be found for example in U.S. patent application Ser. No. 11/762,165 (filed Jun. 23, 2007; disclosing Minimally Invasive Surgical System), U.S. Pat. No. 6,837,883 B2 (filed Oct. 5, 2001; disclosing Arm Cart for Telerobotic Surgical System), and U.S. Pat. No. 6,331,181 (filed Dec. 28, 2001; disclosing Surgical Robotic Tools, Data Architecture, and Use), all of which are incorporated herein by reference.

In FIG. 2, cameras 220L, 220R and combination light source 210 are shown as being external to endoscope 101. However, in one aspect, cameras 220L, 220R and light source 210 are included in the distal tip of endoscope 101, which is adjacent tissue 103; or in the backend housing of endoscope 101.

FIG. 3 is a process flow diagram of one aspect of the imaging operation 300 of system 100. Imaging operation 300 includes two pipelines, a visible image processing pipeline 310 and a hyperspectral image processing pipeline 320. The visible image processing pipeline 310 is similar to prior computer-assisted surgical systems visible image processing pipelines, except visible video sequences 421L_V, 421R_V (FIG. 4) are saved for and used by hyperspectral imaging processing pipeline 320 in one aspect.

In the example of FIG. 3, in the augmented viewing mode, both visible image processing pipeline 310 and hyperspectral image processing pipeline 320 are simultaneously displaying a video output in one aspect. In another aspect, in the augmented viewing mode, only the hyperspectral image processing pipeline 320 is displaying a video output. In either instance, the augmented image processing pipeline 320 outputs features or information in the display that typically cannot be observed in a visible video image sequence.

In response to a user input from display mode select 252 selecting a normal viewing mode, a display selection signal 301 (FIG. 3) indicating the normal viewing mode is provided to a VIEWING MODE check process 302 (FIG. 3) in a user interface 261 that in turn provides a white light illumination active control signal to an ILLUMINATE TISSUE WITH WHITE LIGHT process 303. User interface 261, in one aspect, is generated by a user control module.

In one aspect, the normal viewing mode is a default mode. In this aspect, display mode select 252 would not be used until the surgeon wanted to switch from the normal viewing mode to an augmented viewing mode or from an augmented viewing mode to the normal viewing mode.

ILLUMINATE TISSUE WITH WHITE LIGHT process 303 sends a white light operation command to light controller 215 in combination light source 210. Light controller 215 is illustrated as being located within combination light source 210 for convenience and is not intended to limit the location of light controller 215 to this specific location.

In response to the white light operation command, light controller 215 turns off hyperspectral light illuminator 212, if illuminator 212 is on, and enables visible light illuminator 211 so that tissue 103 is illuminated by white light. Those knowledgeable in the field recognize that instead of turning the power on and off to illuminators 211 and 212, controller 215 could maintain the power always on and direct the output from the illuminators to and away from connector 216 and achieve the same result.

Thus, in the normal viewing mode of operation, ILLUMINATE TISSUE WITH WHITE LIGHT process 303 causes tissue 103 to be illuminated with white light. Visible light from tissue 103 (FIG. 2) is passed by the stereoscopic optical channels in endoscope 101 to image capture system 220. Recall, image capture system 220, in this aspect, includes a left camera 220L that includes a left visible color image capture sensor 221L_V and a right camera 220R that includes a right visible color image capture sensor 221R_V.

Thus, in CAPTURE VISIBLE IMAGE process 304 (FIG. 3), left visible color image capture sensor 221L_V captures a visible left frame and right visible color image capture sensor 221R_V captures a visible right frame. The acquired left and right visible frames include color scenes of the surgical site, e.g., red-green-blue scenes.

Left visible color image capture sensor 221L_V and right visible color image capture sensor 221R_V can each be multiple charge-coupled devices (CCDs) that each captures a different visible color component, a single CCD with different regions of the CCD that capture a particular visible color component, etc. A three-chip CCD sensor is illustrative only. A single CMOS image capture sensor with a color filter array or a three-CMOS color image capture sensor assembly may also be used for each of left visible color image capture sensor 221L_V and right visible color image capture sensor 221R_V.

After the left and right visible frames are acquired, AUGMENTED check process 305 determines whether the viewing mode is augmented or normal. When the viewing mode is augmented, AUGMENTED check process 305 transfers to SAVE VISIBLE IMAGE process 306 that saves the acquired left and right visible frames. When the viewing mode is normal, AUGMENTED check process 305 transfers to TRANSMIT VISIBLE IMAGE process 307.

Thus, in the normal viewing mode of operation, the acquired visible left visible frame and the acquired visible right frame are provided to an image processing module 240 (FIG. 2) in central controller 260 that performs TRANSMIT VISIBLE IMAGE process 307 (FIG. 3). In TRANSMIT VISIBLE IMAGE process 307, any processing of the two acquired visible frames is done so that portion of the surgical site in the field of view of the cameras is accurately reproduced when the scenes captured in the frames are displayed. This processing is the same as was done in prior systems. TRANSMIT VISIBLE IMAGE process 307 sends the processed visible left frame and the processed visible right frame to stereoscopic display 251 and a stereoscopic color scene is displayed in DISPLAY VISIBLE IMAGE process 308 by stereoscopic display 251.

With the exception of AUGMENTED check process 305, the processing in the normal viewing mode of operation is equivalent to the processing in a conventional computer-assisted surgical system and so is known to those knowledgeable in the field. Also, processes 304, 307, and 308 are performed repetitively for each frame so that the surgeon sees a real-time video scene including tissue 103.

During the normal viewing mode of operation, the surgeon is provided with a normal three-dimensional color view of tissue 103. However, the surgeon may wish to see a region or regions of interest in tissue 103 highlighted in the three-dimensional view of tissue 103. For example, the surgeon may which to see diseased portions of tissue and/or a specific tissue, e.g., a tendon or organ, which are not visible or are not clearly visible in the normal three-dimensional color view of tissue 103. Thus, at a time $t_0$ (FIG. 4), the surgeon uses display mode select 252 to switch to the augmented viewing mode of operation with time constant hyperspectral illumination.

Time Constant Hyperspectral Illumination

In response to the user input from display mode select 252, an augmented display selection command indicating an augmented viewing mode with constant hyperspectral illumination is provided to VIEWING MODE check process 302 in user interface 261. In response to the augmented viewing mode with constant hyperspectral illumination command, check process 302, in this aspect, provides an active white light illumination control signal to an ILLUMINATE TISSUE WITH WHITE LIGHT process 303 in visible image processing pipeline 310 and provides an active hyperspectral constant illumination control signal to ILLUMINATE TISSUE WITH HYPERSPECTRAL LIGHT process 321 in hyperspectral image processing pipeline 320.

The acts in visible image processing pipeline 310 were described above, and so are not repeated here for this augmented viewing mode because the acts are the same as described above.

In response to the active hyperspectral constant illumination control signal, ILLUMINATE TISSUE WITH HYPERSPECTRAL LIGHT process 321 sends a constant hyperspectral light operation signal to light controller 215 in combination light source 210. In response to the constant hyperspectral light operation signal, light controller 215 configures hyperspectral light illuminator 212 to provide a time constant spectrum of hyperspectral light to connector 216.

Since ILLUMINATE TISSUE WITH WHITE LIGHT process 303 sends a white light operation signal to light controller 215 in combination light source 210, light controller 215 configures visible light illuminator 211 to provide white light to connector 216. Thus, in this augmented mode, tissue 103 is illuminated with a combination of white light and hyperspectral light.

Light from tissue 103 (FIG. 2) is passed by the stereoscopic optical channels in endoscope 101 to image capture system 220. In one aspect, as explained more completely below, filters are used to select hyperspectral wavelength spectrum(s) captured by cameras 220L, 200R, sometimes referred to as image capture units 220L, 220R.

In this augmented viewing mode of operation, at time $t_0$, CAPTURE VISIBLE IMAGE process 304 (FIG. 3) acquires a first visible left color frame 421L_V_t0 with left visible image capture sensor 221L_V and acquires a first visible right color frame 421R_V_t0 with right visible image sensor 221R_V (FIG. 4). Similarly, at time $t_0$, CAPTURE HYPERSPECTRAL IMAGE process 322 (FIG. 3) acquires a first hyperspectral left frame 421L_HS_t0 with left hyperspectral image capture sensor 221L_HS and acquires a first hyperspectral right frame 421R_HS_t0 with right hyperspectral image capture sensor 221R_HS. CAPTURE VISIBLE IMAGE process 304 and CAPTURE HYPERSPECTRAL IMAGE process 322 are performed substantially simultaneously due to the construction of the image capture units, as discussed more completely below with respect to FIG. 8A, and the synchronization of acts in the capture process of the visible and hyperspectral frames.

As explained previously, first visible left color frame 421L_V_t0 and first visible right color frame 421R_V_t0 captured at time $t_0$ are saved by SAVE VISIBLE IMAGE PROCESS 306 for any augmented viewing mode. SAVE VISIBLE IMAGE PROCESS 306 transfers to PICTURE-IN-PICTURE (PIP) MODE check process 309. Frames saved by SAVE VISIBLE IMAGE PROCESS 306 are available to SPATIAL REGISTRATION process 324.

In one aspect, the user of computer-assisted surgical system 100 uses the user interface to specify a picture-in-picture augmented mode or a search augmented mode. If the user selects picture-in-picture augmented mode, PICTURE-IN-PICTURE (PIP) MODE check process 309 transfers to TRANSMIT VISIBLE IMAGE process 307, and otherwise transfers to CAPTURE VISIBLE IMAGE process 304, which captures another set of visible frames at time $t_1$. Thus, in the picture-in-picture augmented mode, visual image processing pipeline 310 generates the normal surgical site video sequence of frames on display 251. In the search augmented mode, visual image processing pipeline 310 does not generate a surgical site video sequence, and so typically, use of surgical instruments is inhibited or the rate of motion restricted due to the processing delay required to generate a displayed scene.

Returning to hyperspectral image processing pipeline 320, upon completion of CAPTURE HYPERSPECTRAL IMAGE process 322 processing transfers to SAVE HYPERSPECTRAL IMAGE process 323. SAVE HYPERSPECTRAL IMAGE process 323 saves first hyperspectral left frame 421L_HS_t0 and first hyperspectral right frame 421R_HS_t0, and then transfers to SPATIAL REGISTRATION process 324, sometimes referred to a process 324.

As explained above, the resolution of the hyperspectral scene of a hyperspectral frame is, in some cases, less than the resolution of the visible color scene of a visible frame. Thus, to obtain a useful hyperspectral image, it is necessary to capture a plurality of hyperspectral images that can be combined to make a composite hyperspectral image with acceptable resolution. The number of hyperspectral images in the plurality of hyperspectral images depends in part on the output of hyperspectral light illuminator 212.

If hyperspectral light illuminator 212 outputs a time constant spectrum of hyperspectral light, each pixel of the hyperspectral image capture sensor, i.e. each pixel of left hyperspectral image capture sensor 221L_HS and each pixel of right hyperspectral image capture sensor 221R_HS, captures only a portion of the spectrum of the hyperspectral light at the position of the pixel. Thus, the surgical site is scanned so that entire spectrum of the hyperspectral light or at least enough of the entire spectrum can be measured at each location in the scene to form a composite hyperspectral frame having acceptable resolution both spatially and spectrally. Here, acceptable resolution means a resolution so that when the composite hyperspectral image created for time $t_0$ is superimposed on the corresponding visual image captured at time $t_0$, the features which can be derived from and presented in the composite hyperspectral frame are in sufficient detail to be useful to the viewer.

At each location, as the field of view of image capture system 220 is scanned across the surgical site, a hyperspectral frame is captured. At each of these locations, the pose of image capture system 220 is known, i.e., the pose of camera 220L and the pose of camera 220R are known.

The number of hyperspectral frames needed from a scan across the surgical site is determined empirically based on the performance of the algorithm used to extract the features from the raw frames. Specifically, a surgical site is scanned using different numbers of locations at which hyperspectral frames are captured, and for each set of hyperspectral frames, a composite hyperspectral frame is generated, as described more completely below. This produces a set of composite hyperspectral frames. A group of people or an algorithmic or a neural network or other machine learning construct may be asked to select the composite hyperspectral frame or frames or combination of frames that suitably display the feature of interest or from which the features may be derived. In one aspect, the composite hyperspectral frame that required the least number of locations to provide an acceptable image of the feature of interest is selected. Hence, for constant hyperspectral illumination, the number of hyperspectral frames N in a set is empirically determined, and so is known for subsequent cases.

Returning to SPATIAL REGISTRATION process 324, process 324 analyzes the set of N hyperspectral frames, and then processes the N hyperspectral frames to form a composite hyperspectral frame that includes a composite hyperspectral scene of the surgical site. The spatial registration of the hyperspectral frames in the set to one another is done, in one aspect, by first identifying features in each of the hyperspectral frames, and then tracking these features from frame to frame in the set of hyperspectral frames. When the location of a feature, or features, is/are known in some of all of the frames, this permits re-aligning the frames so that the feature, or features, is/are at common location in a composite hyperspectral image. Thus, the tracking of features permits superposition of the set of hyperspectral frames.

In one aspect, SAVE HYPERSPECTRAL IMAGE process 323 transfers processing to a FEATURE EXTRACTION process 325 of SPATIAL REGISTRATION process 324. FEATURE EXTRACTION process 325 identifies features, sometimes referred to as navigational landmarks, in each of the received hyperspectral frames. FEATURE EXTRACTION process 325 transfers to SET check process 326.

Figure 5A:
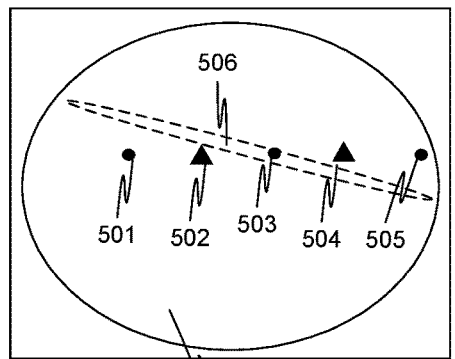
FIG. 5A is an abstract representation a visible surgical site scene contained in a visible frame.

FIG. 5A is an abstract representation a visible surgical site scene contained in a visible frame 510. A feature of interest 506 is not salient in frame 510, e.g., feature 506 is hidden or is not discernable by a human in the visible surgical site scene contained in a visible frame 510. However, navigational landmarks, represented by circles 501, 503, and 505 and triangles 502 and 504, are visible and salient in frame 510. In an actual surgical site scene, normal navigational landmarks could be, for example, a pattern of blood vessels, a pattern of tissue, or patterns of different tissues or small constellations of features created by the intersections of blood vessels or other similar structures. Thus, when a new hyperspectral frame is received by SPATIAL REGISTRATION process 324, FEATURE EXTRACTION process 325 determines the navigational landmarks in that frame.

SET check process 326 determines whether the number of captured hyperspectral frames is equal to N, where N is a non-negative integer number. Number of hyperspectral frames N in a set is the number of hyperspectral frames captured in a channel, and so a set of N hyperspectral frames is captured in each of the left and right channels. If the number of captured hyperspectral frames is less than N, SET check process 326 transfers to CONSTANT ILLUMINATION (Ill.) MODE check process 329, but if the number of captured hyperspectral images equals N, SET check process 326 transfers to TRACK FEATURES process 327 of SPATIAL REGISTRATION process 324 and to RESET SET COUNTER process 328; alternatively, the N hyperspectral frames may be treated as a circular buffer of frames such that the counter is indexing into the N frames and instead of resetting is simply modulo N replacing hyperspectral frames in the stack of N as the new ones arrive.

After capture of hyperspectral image 421L_HS_t0 at time $t_0$, the number of captured hyperspectral images is smaller than N, and so SET check process 326 transfers to CONSTANT ILLUMINATION (Ill.) MODE check process 329. In this example, the hyperspectral illumination spectrum is constant in time, and so CONSTANT ILLUMINATION MODE check process 329 transfers processing to MOVE CAMERA process 330.

MOVE CAMERA process 330 moves camera 220 to a next location for a scan of the surgical site, and then processes 322, 323, 324, and 330 are repeated. Thus, at time $t_1$, CAPTURE HYPERSPECTRAL IMAGE process 322 (FIG. 3) acquires a second hyperspectral left frame 421L_HS_t1 (FIG. 4) with left hyperspectral image capture sensor 221L_HS and acquires a second hyperspectral right frame 421R_HS_t1 with right hyperspectral image capture sensor 221R_HS. CAPTURE VISIBLE IMAGE process 304 is synchronized with CAPTURE HYPERSPECTRAL IMAGE process 322 so that at time $t_1$, CAPTURE VISIBLE IMAGE process 304 (FIG. 3) acquires a second visible left color frame 421L_V_t1 with left visible image capture sensor 221L_V and acquires a second visible right color frame 421R_V_t1 with right visible image capture sensor 221R_V.

Processes 330, 322, 323, 324 are repeated until at time $t_{N-1}$, CAPTURE HYPERSPECTRAL image process 322 (FIG. 3) acquires an Nth hyperspectral left frame 421L_HS_tN−1 with left hyperspectral image capture sensor 221L_HS and acquires an Nth hyperspectral right frame 421R_HS_tN−1 (FIG. 4) with right hyperspectral image capture sensor 221R_HS, and CAPTURE VISIBLE IMAGE process 304 (FIG. 3) acquires an Nth visible left color frame 421L_V_tN−1 with left visible image capture sensor 221L_V and acquires an Nth visible right color frame 421R_V_tN−1 with right visible image capture sensor 221R_V. Since the number of captured hyperspectral frames now equals N, SET check process 326 transfers to TRACK FEATURES process 327 and to RESET SET COUNTER process 328.

Figure 5B:
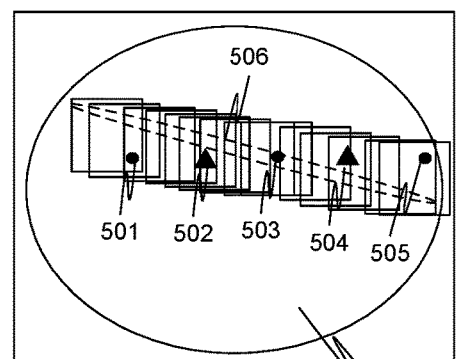
FIG. 5B is an abstract representation of the scan of the surgical site scene of FIG. 5A.

FIG. 5B is an abstract representation of the scan of the surgical site scene of FIG. 5A. Each box in the scene represents one of the hyperspectral frames that are captured. FIG. 5B is not drawn to scale, and a box represents only a captured hyperspectral frame and not the size of the frame. The size of the captured hyperspectral frame is determined, for example, by the size and number of pixels in the hyperspectral image capture sensors in conjunction with the characteristics of the optics creating the image. Captured hyperspectral frames include images of some or all of navigational landmarks 501 to 505.

RESET SET COUNTER process 328 resets the counter for the number of hyperspectral frames captured in a set and transfers processing to CONSTANT ILLUMINATION (Ill.) MODE check process 329. In this example, the output illumination is constant, and so CONSTANT ILLUMINATION MODE check process 329 transfers processing to MOVE CAMERA process 330.

MOVE CAMERA process 330 moves camera 220 for a scan of surgical site, and then processes 322, 323, 324, and 330 are repeated for a second set of captured hyperspectral frames. Thus, at time $t_N$, CAPTURE HYPERSPECTRAL IMAGE process 322 (FIG. 3) acquires a first hyperspectral left frame 421L_HS_tN with left hyperspectral image capture sensor 221L_HS and acquires a first hyperspectral right frame 421R_HS_tN with right hyperspectral image capture sensor 221R_HS in a second set of hyperspectral images. At time $t_N$, CAPTURE VISIBLE IMAGE process 304 (FIG. 3) acquires an N+1 visible left color frame 421L_V_t1 with left visible image capture sensor 221L_V and acquires an N+1 visible right color frame 421R_V_t1 with right visible image capture sensor 221R_V.

Processes 330, 322, 323, 324 are repeated for the second set of hyperspectral images in the same manner as just described for the first set. If the acquisition is performed using the circular buffer technique, then the sets of hyperspectral images always contain the N most recent frames and the above process fills that N deep buffer. Also note that the time intervals between hyperspectral frames may be greater or less than the time interval between visible light frames— there is no fundamental change to the realignment and composition of the images shown to the surgeon.

Recall that upon completion of capture of the first set of hyperspectral images, processing transferred to TRACK FEATURES process 327 of SPATIAL REGISTRATION process 324. The visible navigational landmarks 501 to 505 captured in the hyperspectral frames enable a tissue tracking process to align the spectral data acquired in the hyperspectral frames captured at different points in time to form a composite hyperspectral image for time $t_0$. Since the spatial relationship between the hyperspectral frame captured at time $t_0$ and the visible frame captured at time $t_0$ is known, the composite hyperspectral frame can be superimposed with visible frame 510 that was captured at time $t_0$ even though locations of objects in the hyperspectral surgical site scenes may change slightly with time. Alternatively, features in the hyperspectral images could be aligned to corresponding visible features in the visible image to align each hyperspectral frame to the visible frame. In yet another aspect, features in the hyperspectral images are used to align the hyperspectral images and then the composite hyperspectral frame is aligned to the visible frame. The hyperspectral sensor to visible sensor alignment is known from a camera manufacturer calibration.

Hence, in one aspect, SPATIAL REGISTRATION process 324, features are computer generated using, for example, a scale-invariant feature transform (SIFT), for example, and these computer generated features are used with a visual Simultaneous Localization and Mapping (vSLAM) model, where the features (locations of points) on the surface of the tissue are tracked over time as the tissue moves (due to respiration and heart rate, etc.) and as the camera capturing the frame is tracked in position and orientation. SIFT and VSLAM are not described in detail, because the combination of the two is known. See for example, Niklas Karlsson, Luis Goncalves, Mario E. Munich and Paolo Pirjanian, "The vSLAM Algorithm for Navigation in Natural Environments," Korean Robotics Society Review, Vol. 2. No. 1. pp. 51-67, 2005, which is incorporated by reference.

Additionally, if the camera system is stereoscopic, the additional information from the pair of hyperspectral frames or visible frames captured at each instance in time can be used to improve the tracking of the tissue over time. Each pair of stereoscopic hyperspectral frames or visible frames may be used to create a depth map of the surgical scene. The depth maps provide information about what features are visible with respect to time, and so improves the ability to track some features.

Figure 6:
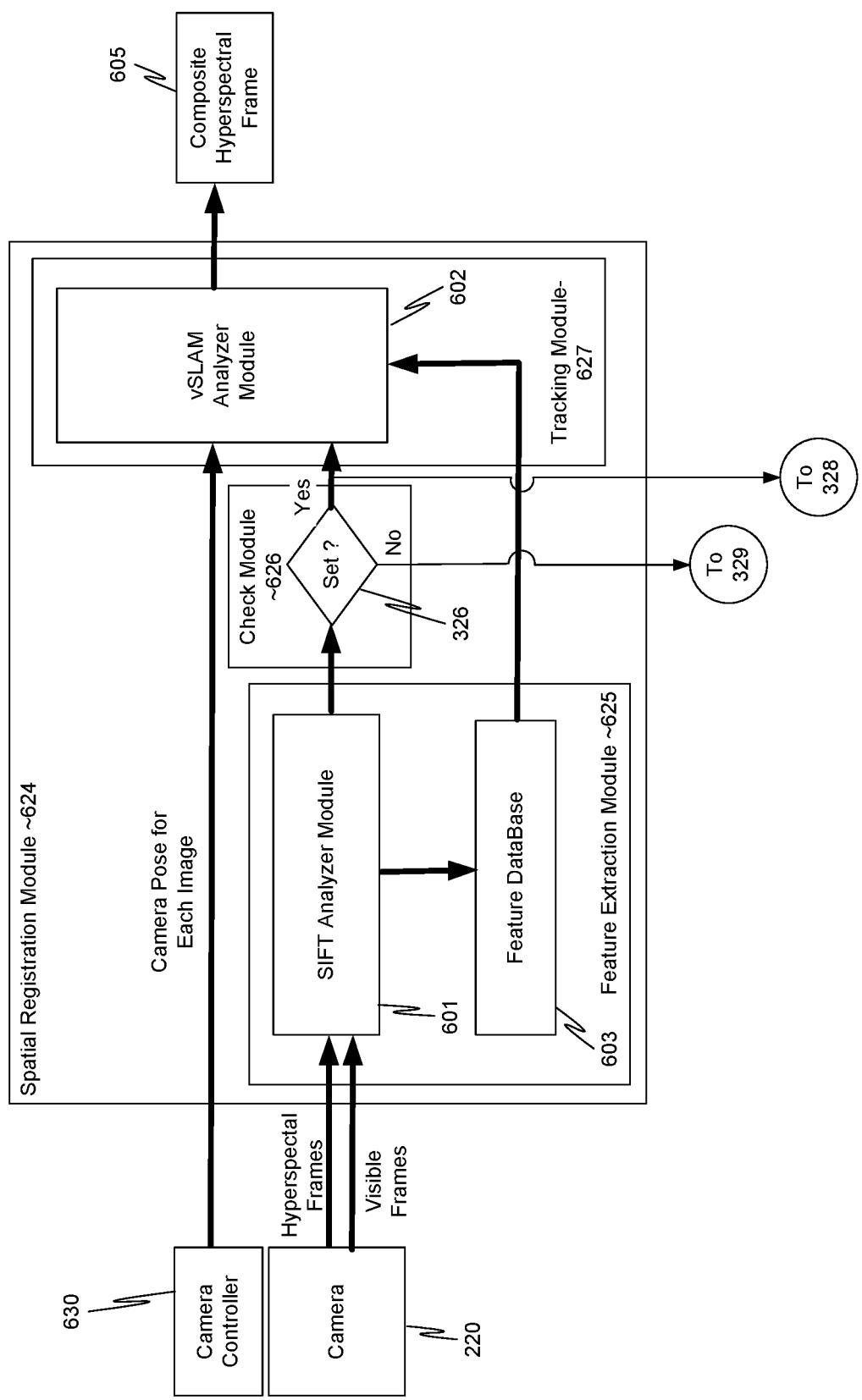
FIG. 6 is a block diagram of one implementation of the SPATIAL REGISTRATION process of FIG. 3.

FIG. 6 is a block diagram of one implementation of a spatial registration module 624 that performs SPATIAL REGISTRATION process 324. A SIFT analyzer module 601 in a feature extraction module 625 receives as input each frame of the set of hyperspectral frames captured by camera 220. SIFT analyzer module 601 detects the locations of features in each of the captured hyperspectral frames in the set, and saves information characterizing the features in landmark database 603. Here, camera 220 is one of camera 220R and camera 220L. Recall that the processing in of the captured left and right hyperspectral frame sets is the same. In this aspect, extraction module 625 performs FEATURE EXTRACTION process 325. Similarly the visual frames are also processed and their features extracted.

Check module 626 in spatial registration module 624 performs SET check process 326, which was previously described.

Camera controller 630 provides vSLAM analyzer module 602 the camera pose for each hyperspectral and visible frame (which may have been captured at different moments in time). vSLAM analyzer module 602 is included in a tracking module 627 of spatial registration module 624. Tracking module 627, in this aspect, performs TRACK FEATURES process 327.

vSLAM analyzer module 602 uses the information in landmark database 603 and tracks the location of the landmarks over time so that the frames in the set can be superimposed to form a composite hyperspectral frame 605 that is output by SPATIAL REGISTRATION process 625. The camera pose information makes the tracking process more robust.

As described above, each of modules 624, 625, 626, 627, 601, and 602 may include hardware, RTL, software that is executed on a processor, firmware, or any combination of these.

Thus, returning to FIG. 3, the result of SPATIAL REGISTRATION process 324 is a composite hyperspectral frame that is formed from the captured set of hyperspectral frames. The pixels in the hyperspectral frame correspond to pixels in the visible frame captured at time $t_0$ so that when the composite hyperspectral frame is superimposed on the visible frame captured at time $t_0$, feature 506 is in the correct location and is visible. The features in the composite hyperspectral frame are highlighted relative to the visible frame when the two frames are superimposed. For example, the features in the composite hyperspectral frame can be false colored using a color not typically seen in a surgical site scene, e.g., green. In another aspect, the combination visual and hyperspectral image is processed, for example, by a machine learning classifier or similar process to identify specific tissue types, etc.

The hyperspectral frames may be further processed in some way in conjunction with the visible frames to produce a composite output which results in added visual saliency of features which are hard for some surgeons to see in the image some of the time. For example, the composite image might highlight a structure which does not appear in the visual images at all and as such, provides information to the surgeon. These enhanced images created from the hyperspectral data and the visible image may reveal information which a very experienced surgeon could determine but that a resident or fellow might have difficulty determining.

Upon completion, SPATIAL REGISTRATION process 324 transfers to an optional SPECIAL CHARACTERISTICS DETERMINATION process 331, sometimes referred to as process 331. Process 331 is optional, because the process is utilized when a stereoscopic endoscope is used and when parameters such as absolute reflectance or emission of the light from the tissue are needed to interpret information in the images to be displayed, the displayed scenes.

Hence, either SPATIAL REGISTRATION process 324 or SPECIAL CHARACTERISTICS process 331 transfers to TRANSMIT VISIBLE AND COMPOSITE IMAGES process 332, sometimes referred to as process 332. Process 332 sends the visible frames 421R_V_t0 and 421L_V_t0 and the composite hyperspectral frame for time $t_0$ to stereoscopic display 251, or alternatively sends the superposition of the visible and hyperspectral images in each of the two channels. The image displayed by stereoscopic display in DISPLAY VISIBLE AND COMPOSITE IMAGES process 333 depends on the particular augmented display mode selected by the user of system 100.

For example, in a search only augmented mode, PIP MODE check process 309 does not transfer to TRANSMIT VISIBLE IMAGE process 307, and so in DISPLAY VISIBLE AND COMPOSITE IMAGES process 333, a stereoscopic color visible scene including tissue 103 superimposed with a composite hyperspectral scene including feature of interest 506 is presented on stereoscopic display 251. The initial display on stereoscopic display is delayed in this mode to provide for the processing time required by hyperspectral image processing pipeline 320, e.g., about 100 to 500 milliseconds, and then a continuous video sequence is presented to the user of system 100.

Figure 5C:
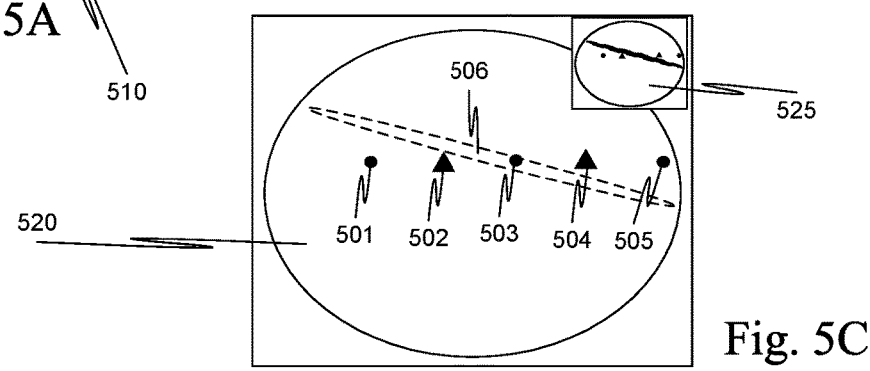
FIG. 5C is an illustration of a picture within a picture for the surgical site scene of FIG. 5A.

In another aspect, in a picture within a picture augmented mode, PIP MODE check process 309 transfers to TRANSMIT VISIBLE IMAGE process 307 that in turn transfers to DISPLAY VISIBLE IMAGE process 308, which displays a video sequence of visible scenes including tissue 103 as main display scene 520 (FIG. 5C) on stereoscopic display 251. DISPLAY VISIBLE AND COMPOSITE IMAGES process 333 presents a stereoscopic color visible scene including tissue 103 superimposed with a composite hyperspectral scene including feature of interest 506 as a picture within a picture scene 525 on stereoscopic display 251.

Since hyperspectral image processing pipeline 320 requires more processing time than visible image processing pipeline 310, the visible image of tissue 103 with the superimposed composite image in the picture within the picture trails in time main display scene 520. However, the visible image in the picture within a picture is the same as the visible image that appeared in main display scene 520. For example, frames 421R_V_t0 and 421L_V_t0 are displayed in main display scene 520 and then sometime later, frames 421R_V_t0 and 421L_V_t0 superimposed with the composite hyperspectral frame for time $t_0$ are displayed in picture within a picture scene 525. However, since the visible image scenes in the two displays are the same, the slight delay in the picture within a picture scene is acceptable to the user of system 100.

Time Sequential Hyperspectral Illumination

In the previous example of hyperspectral image processing pipeline 320, it was assumed that the hyperspectral illumination was constant in time and spectrum, and that the camera was scanned across the scene to capture hyperspectral frames that could be combined to form a composite frame even though parts of the scene that was captured moved with respect to time. However, in another example, the spectrum of the hyperspectral illumination changes sequentially with time and a hyperspectral frame is captured for each time sequential waveband of hyperspectral illumination or alternatively for each tine sequential wavelength of hyperspectral illumination. As used herein, a waveband of hyperspectral light is a spectrum of hyperspectral light. If a waveband includes only a single wavelength, the waveband (typically a range of wavelengths) and the wavelength are the same thing. Again, the aspects of the scene being captured can move with time and so while the same scene may be captured in each frame, the location of elements within the captured scenes can change from frame to frame.

Figure 7:
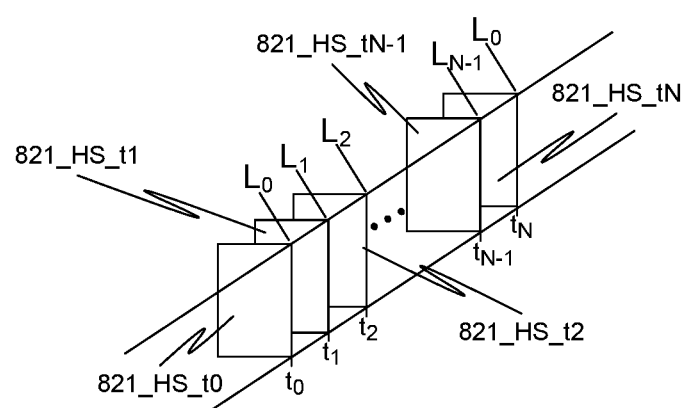
FIG. 7 is a representation of hyperspectral frames captured using time sequential hyperspectral illumination.

Prior to considering hyperspectral image processing pipeline 320 with time sequential illumination, FIG. 7 is an illustration of the sequence of hyperspectral frames captured via hyperspectral image processing pipeline 320. If a stereoscopic image capture system is used, the sequence of frames in FIG. 7 represents both the left and right hyperspectral frames that are captured. At time $t_0$, tissue 103 is illuminated with hyperspectral light waveband $L_0$ and hyperspectral light from tissue 103 is captured in frame 821_HS_t0. At time $t_1$, tissue 103 is illuminated with hyperspectral light waveband $L_1$ and hyperspectral light from tissue 103 is captured in frame 821_HS_t1. At time $t_2$, tissue 103 is illuminated with hyperspectral light waveband $L_2$ and hyperspectral light from tissue 103 is captured in frame 821_HS_t2. At time $t_{N-1}$, tissue 103 is illuminated with hyperspectral light waveband $L_{N-1}$ and hyperspectral light from tissue 103 is captured in frame 821_HS_tN−1. At time $t_N$, tissue 103 is illuminated with hyperspectral light waveband $L_0$ and hyperspectral light from tissue 103 is captured in frame 821_HS_tN.

Here, the adjectives, first, second, third, . . . , Nth in first hyperspectral light waveband $L_0$, second hyperspectral light waveband $L_1$, third hyperspectral light waveband $L_2$, . . . , and Nth hyperspectral light waveband are not meant to imply any ordering of the wavelengths in the wavebands or any ordering of the wavebands with respect to wavelength, but rather that different spectrums of hyperspectral light are used. Also, as explained below, each hyperspectral frame is captured substantially simultaneously with a visible color frame. The meaning of substantially simultaneously is the same as described above.

Thus, in this example N wavebands are used, where N is an integer number equal to or larger than two. The number N of sequential wavebands used is known, and typically depends on the tissue of interest. Typically, less than ten different sequential wavebands are used, but more than ten can also be used. For example, in one aspect, three wavebands are used to image ureters. See U.S. Patent Application No. 62/092,651 (filed on 16 Dec. 2014, and disclosing "Ureter Detection Using Waveband Selective Imaging"), which is incorporated herein by reference in its entirety.

Returning to FIG. 3, in response to the user input from display mode select 252, an augmented display selection command indicating an augmented viewing mode with time sequential hyperspectral illumination is provided to VIEWING MODE check process 302 in user interface 261. In response to augmented viewing mode with time sequential hyperspectral illumination command, check process 302, in this aspect, provides an active white light illumination control signal to an ILLUMINATE TISSUE WITH WHITE LIGHT process 303 in visible image processing pipeline 310 and provides an active hyperspectral time sequential illumination active signal to ILLUMINATE TISSUE WITH HYPERSPECTRAL LIGHT process 321 in hyperspectral image processing pipeline 320.

The acts in visible image processing pipeline 310 were described above, and so are not repeated here for this augmented viewing mode because the acts are the same as described above.

In response to the hyperspectral time sequential illumination control signal, ILLUMINATE TISSUE WITH HYPERSPECTRAL LIGHT process 321 sends a time sequential hyperspectral light operation signal to light controller 215 in combination light source 210. In response to the time sequential hyperspectral light operation signal, light controller 215 configures hyperspectral light illuminator 212 to provide a first waveband $L_0$ of hyperspectral light to connector 216.

Since ILLUMINATE TISSUE WITH WHITE LIGHT process 303 sends a white light operation signal to light controller 215 in combination light source 210, light controller 215 configures visible light illuminator 211 to provide white light to connector 216. Thus, in this augmented mode, tissue 103 is illuminated with a combination of white light and a first waveband of hyperspectral light.

Light from tissue 103 (FIG. 2) is passed by the stereoscopic optical channels in endoscope 101 to image capture system 220. In this augmented viewing mode of operation, at time $t_0$, CAPTURE VISIBLE IMAGE process 304 (FIG. 3) acquires a first visible left color frame 421L_V_t0 with left visible image capture sensor 221L_V and acquires a first visible right color frame 421R_V_t0 with right visible image capture sensor 221R_V. Similarly, at time $t_0$, CAPTURE HYPERSPECTRAL IMAGE process 322 (FIG. 3) acquires a first hyperspectral left frame 421L_HS_t0 with left hyperspectral image capture sensor 221L_HS and acquires a first hyperspectral right frame 421R_HS_t0 (FIG. 4) with right hyperspectral image capture sensor 221R_HS. CAPTURE VISIBLE IMAGE process 304 and CAPTURE HYPERSPECTRAL IMAGE process 322 are performed substantially simultaneously due to the construction of the image capture units, as discussed more completely below with respect to FIG. 10B, and the synchronization of acts in the capture process of the visible and hyperspectral frames.

As explained previously, first visible left color frame 421L_V_t0 and first visible right color frame 421R_V_t0 captured at time $t_0$ are saved by SAVE VISIBLE IMAGE PROCESS 306 for any augmented viewing mode. SAVE VISIBLE IMAGE PROCESS 306 transfers to PICTURE-IN-PICTURE (PIP) MODE check process 309. Frames saved by SAVE VISIBLE IMAGE PROCESS 306 are available to SPATIAL REGISTRATION process 324. PICTURE-IN-PICTURE (PIP) MODE check process 309 operates as described above, and so that description is not repeated here.

Returning to hyperspectral image processing pipeline 320, upon completion of CAPTURE HYPERSPECTRAL IMAGE process 322 processing transfers to SAVE HYPERSPECTRAL IMAGE process 323. SAVE HYPERSPECTRAL IMAGE process 323 saves first hyperspectral left frame 421L_HS_t0 and first hyperspectral right frame 421R_HS_t0, and then transfers to FEATURE EXTRACTION process 325.

Process 325 is equivalent to the description above, in one aspect, and so that description is not repeated here. FEATURE EXTRACTION process 325 transfers processing to SET check process 326.

Again, the number N of hyperspectral frames that are needed to make up a set is known. As explained above, the resolution of the hyperspectral scene of a hyperspectral frame may be much less than the resolution of the visible color scene of a visible frame. Thus, in such a case, to obtain a clinically useful hyperspectral image, it is necessary to capture a plurality of hyperspectral images that can be combined to make a composite hyperspectral image with acceptable resolution. The number of hyperspectral images in the plurality of hyperspectral images depends on the number N of illumination wavebands used.

In this aspect, hyperspectral light illuminator 212 outputs wavebands of hyperspectral light in a time sequence, e.g., a first waveband $L_0$ at time $t_0$, a second waveband $L_1$ at time $t_1$, etc., the number of hyperspectral images in the set of hyperspectral images is equal to the number N of time sequential illumination wavebands output by hyperspectral light illuminator 212. If hyperspectral light illuminator 212 outputs different wavebands of hyperspectral light in a time sequence, e.g., a first waveband $L_0$ at time $t_0$, a second waveband $L_1$ at time $t_1$, etc., and the field of view of camera 220 is scanned over the surgical site for each waveband, the number of hyperspectral images in a set of hyperspectral images for each waveband is empirically determined in a manner equivalent to that described for a time constant output from hyperspectral light illuminator 212. In this aspect, there are two numbers to control. The first number is the number m of hyperspectral frames captured in the spatial scan of the surgical site for each waveband, and a second number k is the number of time sequential wavebands used. In this aspect, a composite hyperspectral frame is formed using the m hyperspectral frames, in a manner equivalent to the constant illumination example, for each of the wavebands. This produces k composite hyperspectral frames. The k composite frames are then superimposed, using the registration process for time sequential illumination, to form a final composite image.

For time sequential hyperspectral illumination without a spatial scan, the number of hyperspectral frames N in a set is known, and SET check process 326 determines whether the number of captured hyperspectral frames is equal to N, where N is a non-negative integer number. Number of hyperspectral frames N in a set is again the number of hyperspectral frames captured in a channel, and so a set of N hyperspectral frames is captured in each of the left and right channels. If the number of captured hyperspectral frames is less than N, SET check process 326 transfers to CONSTANT ILLUMINATION (Ill.) MODE check process 329, but if the number of captured hyperspectral images equals N, SET check process 326 transfers to TRACK FEATURES process 327 and to RESET SET COUNTER process 328.

After capture of hyperspectral image 421L_HS_t0 at time $t_0$, the number of captured hyperspectral images is smaller than N, and so SET check process 326 transfers to CONSTANT ILLUMINATION (Ill.) MODE check process 329. In this example, the output illumination is time sequential, and so CONSTANT ILLUMINATION MODE check process 329 transfers processing to ILLUMINATE TISSUE WITH HYPERSPECTRAL LIGHT process 321.

ILLUMINATE TISSUE WITH HYPERSPECTRAL LIGHT process 321, in one aspect, uses the value of the set counter to determine the waveband to illuminate tissue 103. Hence, in this example, ILLUMINATE TISSUE WITH HYPERSPECTRAL LIGHT process 321 sends a time sequential hyperspectral light operation signal for a second waveband $L_1$ to light controller 215 in combination light source 210. In response to the time sequential hyperspectral light operation signal for second waveband $L_1$, light controller 215 configures hyperspectral light illuminator 212 to provide second waveband $L_1$ of hyperspectral light to connector 216. Thus, tissue 103 is illuminated with second waveband $L_1$ of hyperspectral light.

Upon completion of ILLUMINATE TISSUE WITH HYPERSPECTRAL LIGHT process 321, processes 322, 323, 324, 325, and 326 are repeated. Thus, at time $t_1$, CAPTURE HYPERSPECTRAL IMAGE process 322 (FIG. 3) acquires a second hyperspectral left frame 421L_HS_t1 with left hyperspectral image capture sensor 221L_HS and acquires a second hyperspectral right frame 421R_HS_t1 with right hyperspectral image capture sensor 221R_HS. CAPTURE VISIBLE IMAGE process 304 is synchronized with CAPTURE HYPERSPECTRAL IMAGE process 322 so that time $t_1$, CAPTURE VISIBLE IMAGE process 304 (FIG. 3) acquires a second visible left color frame 421L_V_t1 with left visible image capture sensor 221L_V and acquires a second visible right color frame 421R_V_t1 with right visible image capture sensor 221R_V.

Processes 329, 321, 322, 323, 325, and 326 are repeated until at time $t_{N-1}$, CAPTURE HYPERSPECTRAL image process 322 (FIG. 3) acquires an Nth hyperspectral left frame 421L_HS_tN−1 with left hyperspectral image capture sensor 221L_HS and acquires an Nth hyperspectral right frame 421R_HS_tN−1 with right hyperspectral image capture sensor 221R_HS, and CAPTURE VISIBLE IMAGE process 304 (FIG. 3) acquires an Nth visible left color frame 421L_V_tN−1 with left visible image capture sensor 221L_V and acquires an Nth visible right color frame 421R_V_tN−1 with right visible image capture sensor 221R_V. Since the number of captured hyperspectral frames now equals N, SET check process 326 transfers to TRACK FEATURES process 327 and to RESET SET COUNTER process 328.

RESET SET COUNTER process 328 resets the counter for the number of hyperspectral frames captured in a set and transfers processing to CONSTANT ILLUMINATION (Ill.) MODE check process 329. Note that process 328 is used for ease of discussion and is not intended to be required. As indicated above, if a circular buffer is used, it is not necessary to track the number of captured frames. Also, if a rotating filter is used or control logic is used in combination light source 200 that recycles after N events, maintaining and resetting a counter would not be necessary.

In this example, the output illumination is time sequential, and so CONSTANT ILLUMINATION MODE check process 329 transfers processing to ILLUMINATE TISSUE WITH HYPERSPECTRAL LIGHT process 321. ILLUMINATE TISSUE WITH HYPERSPECTRAL LIGHT process 321 sends a time sequential hyperspectral light operation signal for waveband $L_0$ to light controller 215 in combination light source 210. In response to the time sequential hyperspectral light operation signal for waveband $L_0$, light controller 215 configures hyperspectral light illuminator 212 to provide first waveband $L_0$ of hyperspectral light to connector 216. Thus, at time $t_N$, CAPTURE HYPERSPECTRAL IMAGE process 322 (FIG. 3) acquires a first hyperspectral left frame 421L_HS_tN with left hyperspectral image capture sensor 221L_HS and acquires a first hyperspectral right frame 421R_HS_tN with right hyperspectral image capture sensor 221R_HS in a second set of hyperspectral images. At time $t_N$, CAPTURE VISIBLE IMAGE process 304 (FIG. 3) acquires an N+1 visible left color frame 421L_V_t1 with left visible image capture sensor 221L_V and acquires an N+1 visible right color frame 421R_V_t1 with right visible image capture sensor 221R_V. Processes 322, 323, 324 are repeated, as needed, for the second set of hyperspectral images in the same manner as just described for the first set.

Recall that upon completion of capture of the first set of hyperspectral images, processing also transferred to TRACK FEATURES process 327. TRACK FEATURES process 327 through DISPLAY VISIBLE AND COMPOSITE IMAGES process 333 function as previously described, and so that description is not repeated here.

The above example assumed that SPATIAL REGISTRATION process 324 for time sequential hyperspectral illumination and for time constant hyperspectral illumination was the same process. This is illustrative only and is not intended to be limiting.

In another aspect, a different SPATIAL REGISTRATION process 324 is used for time sequential hyperspectral illumination. In this aspect, a stereoscope endoscope is used, and so a hyperspectral depth map can be formed for each hyperspectral illumination waveband. Thus, using the stereo correspondence between the left and right images. N hyperspectral depth maps are created.

Since the camera pose does not change for the N hyperspectral depth maps, the N hyperspectral depth maps can be used to align the N hyperspectral frames so that these frames can be combined to form the composite hyperspectral frame. The alignment may be accomplished by finding best matches between the depth maps using a minimization process, which finds the closest match by minimizing the sum of squares distance between the point clouds. For example, an iterative closest point process could be used. The composite hyperspectral frame is superimposed on the visible frame in the same way that was described above for time constant illumination.

Image Capture Unit for Time Constant Illumination

Figures 8A, 8B, 8C:
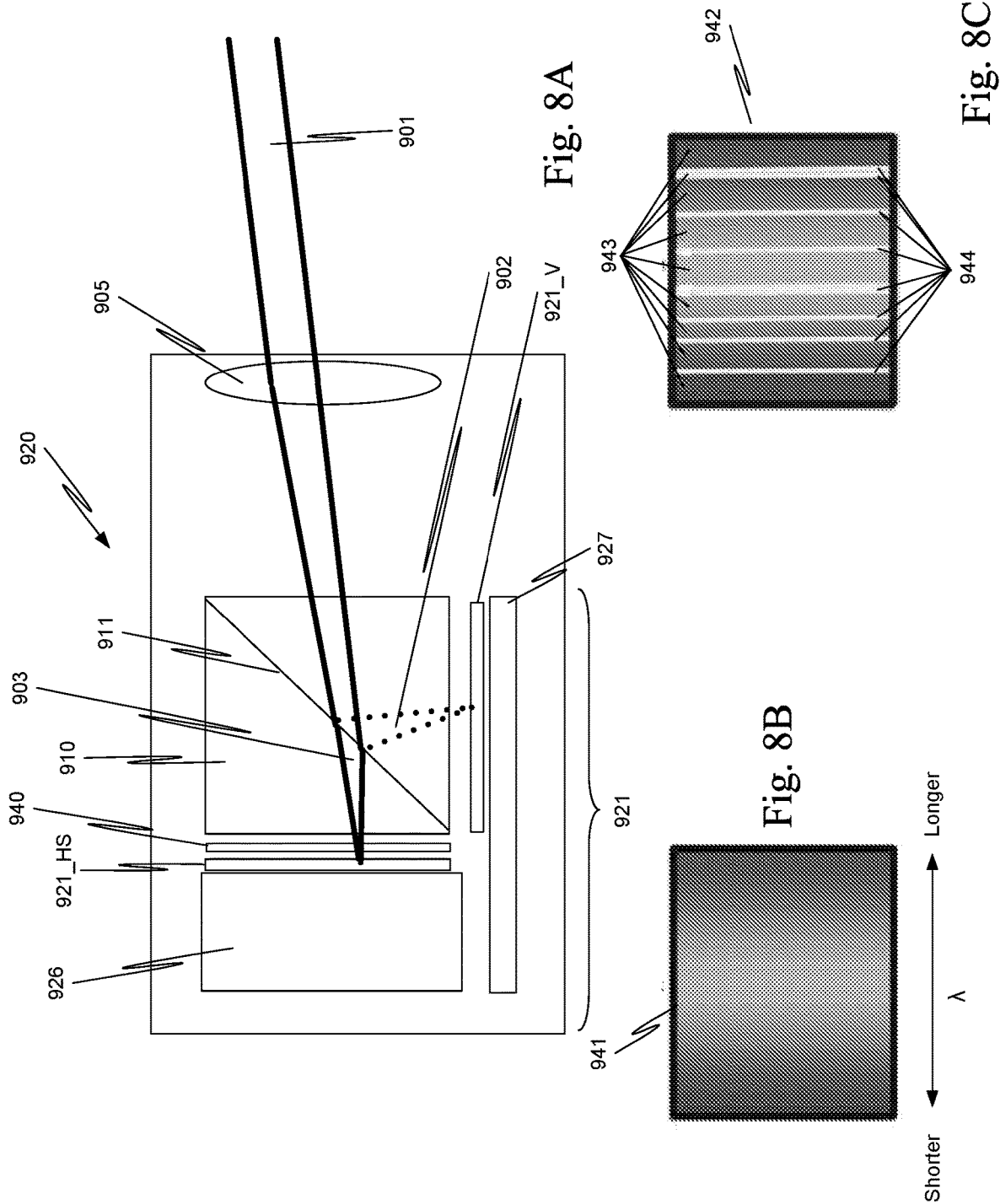
FIG. 8A is a diagram of a camera used with time constant hyperspectral illumination, which simultaneously captures a visible frame and a hyperspectral frame.
FIG. 8B is an illustration of a first type of filter suitable for use in the camera of FIG. 8A.
FIG. 8C is an illustration of a second type of filter suitable for use in the camera of FIG. 8A.

FIG. 8A is an illustration of one aspect of an image capture unit 920 suitable for use as cameras 220L and 220R with a time constant hyperspectral illumination source and a white light illumination source. Light from one or more illumination channels in endoscope 101 illuminates tissue 103 in this example. While it not shown in FIG. 8A, one or more surgical instruments within the field of view of endoscope 101 may also be illuminated via light from the illumination channel or channels. The use of an illumination channel or channels in an endoscope is illustrative only and is not intended to be limiting in the various examples presented in this description. The illumination may be provided by an illumination source in the endoscope or by some other apparatus that is internal or external to the endoscope.

Light reflected from tissue 103 and any fluorescence are received by lens assembly 905 as light 901. Lens assembly 905 may include one of more optical components that direct the received light to sensor assembly 921. Note that lens assembly does not include any type of slit for processing the hyperspectral light. In some aspects, lens assembly 905 is folded.

Light from lens assembly 905 passes to sensor assembly 921. In some aspects, lens assembly 905 does not correct for longitudinal color.

Within sensor assembly 921, the light is received by a beam splitter 911 arranged on the diagonal of a beam splitter cube 910 in this aspect. In one aspect, beam splitter 911 is implemented as a buried coated surface.

The use of a beam splitter cube is illustrative only and is not intended to be limiting. For example, beam splitter 911 could be a filter floating in space.

Beam splitter 911 directs a first portion 902 of light received from lens assembly 905 to visible color image capture sensor 921_V and directs a second portion 903 of light received from lens assembly 905 to registration assistance filter assembly 940, sometimes referred to as filter assembly 940. In the example of FIG. 8A, beam splitter 911 reflects first portion 902 of the light received from lens assembly 905 to visible color image capture sensor 921_V and transmits second portion 903 of light received from lens assembly 905 to filter assembly 940. In each of the aspects described herein, the light is directed onto a surface of an image capture sensor and so for brevity it is said that the light is directed onto the image capture sensor.

The wavelengths of light in first portion 902 of light and in second portion of light 903 are determined by the characteristics of beam splitter 911. In one example, beam splitter 911 is configured so that first portion 902 of light is a first portion of visible light received from lens assembly 905, and second portion 903 of light is a combination of a second portion of the visible light received from lens assembly 905 and hyperspectral light received from lens assembly 905. In one example, beam splitter 911 is configured so that first portion 902 is visible light received from lens assembly 905, e.g., light with wavelengths 700 nanometers (nm) and smaller, and second portion of light 903 is a combination of visible light and hyperspectral light received from lens assembly 905, e.g., light with wavelengths longer than 700 nanometers and smaller than or equal to 2.4 micrometers.

First portion 902 of the visible light is focused on visible color image capture sensor 921_V. In one aspect, visible color image capture sensor 921_V captures light having wavelengths in the range of 400 nanometers to 700 nanometers. For example, visible color image capture sensor 921_V is a small pixel CMOS image capture sensor with a Bayer red-green-blue color filter array or a red-green-blue-white color filter array. Visible color image capture sensor 921_V, sometimes referred to as sensor 921_V, is coupled to mechanicals and electronics 927. Mechanicals and electronics 927 include mechanicals for holding sensor 921_V and electronics connected to sensor 921_V.

Second portion 903 of light from lens assembly 905 is focused on hyperspectral image capture sensor 921_HS. Hyperspectral image capture sensor 921_HS includes rows and columns of pixels that make up a frame. Thus, hyperspectral image capture sensor 921_HS captures a frame of information, and not only a row or a column of information at one time as in some prior art hyperspectral cameras.

In one aspect, hyperspectral image capture sensor 921_HS captures light having wavelengths in the range of 700 nanometers to 2.4 micrometers. The range of wavelengths captured is dependent on the characteristics of filter assembly 940, which is described more completely below. Hyperspectral image capture sensor 921_HS is a monochrome large pixel image capture sensor, e.g., an InGsAs sensor with 5 to 20 micrometer pixels or an HgCdTe sensor with similarly sized pixels.

Hyperspectral image capture sensor 921_HS and visible color image capture sensor 921_V can be implemented with different semiconductor technologies, may have different or the same shutters, e.g., a rolling shutter for visible color image capture sensor 921_V and a global shutter for hyperspectral image capture sensor 921_HS. The shutter methodology is a characteristic of the pixel implementation in the semiconductor process chosen. Image sensors 921_V and 921_HS can be placed at different distances from the back of lens 905 because the location of the image sensors is independent—the gap between prism 910 and image sensor 921_V does not need to be equal to the distance from prism 910 to image sensor 921_HS thus, each may be can be focused independently. As the semiconductor characteristics likely differ, image sensors 921_HS and 921_V likely have different pixel sizes. If one imager's active area is smaller than the other, the image for that sensor will cover a portion of the image seen by the other sensor.

Hyperspectral image capture sensor 921_HS, sometimes referred to as sensor 921_HS or image sensor 921_HS, is coupled to mechanicals, cooling, and electronics 926. Mechanicals, cooling, and electronics 926 include mechanicals for holding sensor 921_HS, cooling for sensor 921_HS, and electronics connected to sensor 921_HS.

As mentioned above, the light incident on hyperspectral image capture sensor 921_HS passes through filter assembly

940. In one aspect, filter assembly 940 includes a first notch filter 941. Notch filter 941 is linearly variable, for example, over the width, e.g., on the left side of filter 941, say nine hundred nanometer wavelength ($\lambda$) light is transmitted and on the right side of filter 941, say twelve hundred nanometer wavelength light is transmitted.

In another aspect, filter assembly 940 includes a second notch filter 942. Notch filter 942 includes two pluralities of stripes—a first plurality of stripes 943 that are represented by dark stripes and a second plurality of stripes 944 that are represented white stripes. Each of first plurality of stripes 943 passes, i.e., transmits, a waveband of hyperspectral light and blocks another waveband of light. Each of the dark stripes can pass a different waveband of hyperspectral light, or alternatively some of the strips can pass the same waveband of hyperspectral light. For example, the pattern could be 12342233441111114123, etc. where each different digit represents a different waveband of hyperspectral light. Thus, in this example four different wavebands of hyperspectral light are passed to sensor 921_HS by notch filter 942. Further, the stripes in plurality of stripes 943 do not have to be in any specific order with respect to wavelength. Also, the stripes in plurality of stripes 943 are not required to have a constant width. In another aspect, clear stripes are made on linearly variable notch filter 941 to form notch filter 942.

Each of second plurality of stripes 944 is clear so that second plurality of stripes 944 passes, i.e., transmits, visible light. The stripes in second plurality of stripes 944 are not required to have a constant width. The visible light that is captured by hyperspectral image capture sensor 921_HS is used in spatial registration of the hyperspectral frames to the corresponding visible frame, as described previously. Stripes in second plurality of stripes 944 can be in a random pattern, in a regular pattern, or in a pattern dictated by the assembly process used to make the desired notch filter.

Some of the stripes in first plurality of strips 942 can be black stripes, which do not transmit any light. The black stripes provide a local black level in the captured frame. While in FIG. 8C, the stripes are shown as being vertical stripes, the stripes can be horizontal, vertical, or formed by a random pattern of dots.

Figure 9:
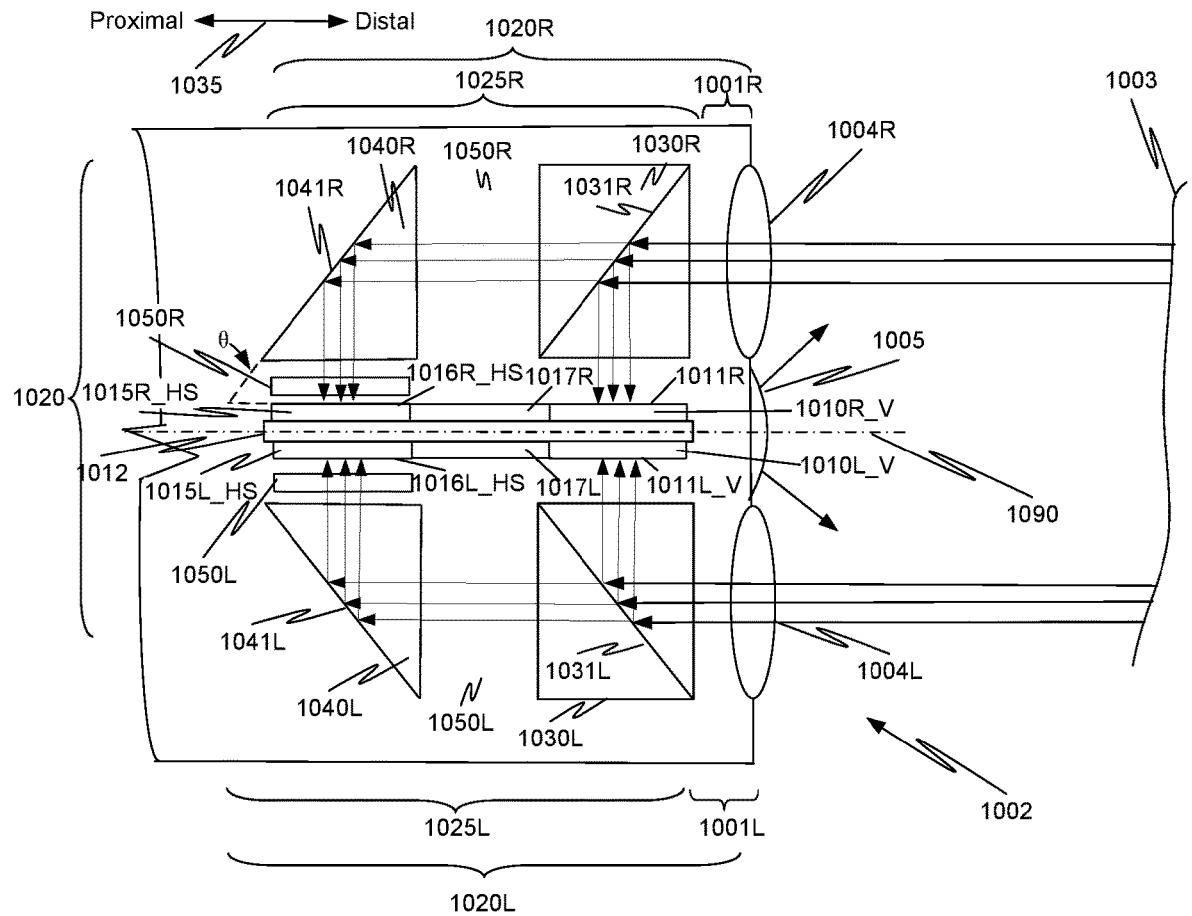
FIG. 9 is a diagram of another camera used with time constant hyperspectral illumination, which simultaneously captures a visible frame and a hyperspectral frame.

FIG. 9 is a block diagram of a distal end of a stereoscopic endoscope 1002 that includes a stereoscopic camera 1020 suitable for use as camera 220. Camera 1020 is used with a time constant hyperspectral illumination source and a white light illumination source.

Stereoscopic camera 1020 includes a left image capture unit 1020L, sometimes referred to as camera 1020L, a right image capture unit 1020R, sometimes referred to as camera 1020R and an illumination channel 1005. Each image capture unit 1020R, 1020L includes a lens assembly 1001R, 1001L and a sensor assembly 1025R, 1025L. Sensor assembly 1025R, 1025L is positioned to receive light that passes through lens assembly 1001R, 1001L. Each sensor assembly 1025R, 1025L includes a prism assembly 1030R, 1030L, a reflective assembly 1040R, 1040L and, in this aspect, coplanar image capture sensors (1010R_V, 1015R_HS), (1010L_V, 1015L_HS), in one aspect. Stereoscopic endoscope 1002 is an example of stereoscopic endoscope 101.

As illustrated in FIG. 9, each stereoscopic channel in a distal end of stereoscopic endoscope 1002, sometimes referred to as endoscope 1002, has the same component configuration. In this FIG. 9 aspect, image capture unit 1020L (for the left stereoscopic channel) and image capture unit 1020R (for the right stereoscopic channel) are symmetric with reference to a plane that intersects centerline longitudinal axis 1090 of endoscope 1002 (i.e., they are positioned as mirror images of each other). As indicated by arrow 1035, the distal direction is towards tissue 1003 and the proximal direction is away from tissue 1003.

Light from one or more illumination channels 1005 in endoscope 1002 illuminates tissue 1003 in this example. While it is not shown in FIG. 9, one or more surgical instruments within the field of view of endoscope 1002 may also be illuminated via light from illumination channel 1005. The use of an illumination channel in an endoscope is illustrative only and is not intended to be limiting in the various examples presented in this description. The illumination may be provided by an illumination source in the endoscope or by some other apparatus that is internal or external to the endoscope.

Light reflected from tissue 1003 and any fluorescence are received by lens assembly 1001L and 1001R. Lenses 1004L and 1004R in lens assembly 1001L and 1001R, respectively, may include one of more optical components that direct the received light to sensor assembly 1025L and sensor assembly 1025R, respectively. In other aspects, lens assembly 1001L and 1001R are folded.

Light from lenses 1004L and 1004R passes to sensor assemblies 1025L, 1025R, respectively. Within sensor assemblies 1025L, 1025R, the light is received by beam splitters 1031L and 1031R, respectively in beam splitter cubes 1030L, 1030R. In one aspect, each of beam splitters 1031L and 1031R is implemented as a buried coated surface 1031L, 1031R. As explained above, the coating or coatings on each of beam splitters 1031L, 1031R is selected to provide a particular functionality. The characteristics of the buried coated surface are equivalent to the characteristics described above for beam splitter 911.

Beam splitter 1031L directs a first portion of the received light onto a first visible color image capture sensor 1010L_V, e.g., onto a surface 1011L_V of visible color image capture sensor 1010L_V, in image capture unit 1020L and directs a second portion of the received light to reflective assembly 1040L. Similarly, beam splitter 1031R directs a first portion of the received light onto a second visible color image capture sensor 1010R_V, e.g., onto a surface 1011R_V of visible color image capture sensor 1010R_V, in image capture unit 1020R and directs a second portion of the received light to reflective assembly 1040R.

The light from beam splitters 1031L and 1031R is received by reflective assemblies 1040L and 1040R, respectively. Reflective unit 1040L directs the received light to a first registration assistance filter assembly 1050L, sometimes referred to as filter assembly 1050L. The light that passes through a filter in filter assembly 1050L is focused on a hyperspectral image capture sensor 1015L_HS, e.g., reflective unit 1040L focuses the received light onto a surface 1016L of hyperspectral image capture sensor 1015L_HS in image capture unit 1020L. Similarly, reflective unit 1040R directs the received light to a second registration assistance filter assembly 1050R, sometimes referred to as filter assembly 1050R. The light that passes through a filter in filter assembly 1050R is focused on a hyperspectral image capture sensor 1015R_HS, e.g., reflective unit 1040R focuses the received light onto a surface 1016R_HS of hyperspectral image capture sensor 1015R_HS in image capture unit 1020R. In each of the aspects described herein, the light is directed onto a surface of an image capture sensor and so for brevity it is said that the light is directed onto the image capture sensor.

Each of reflective assemblies 1040L and 1040R includes a reflective surface 1041L, 1041R, e.g., a mirror surface, which reflects the received light. In the example of FIG. 9, reflective assemblies 1040L and 1040R are each implemented as a prism with one face having a reflective coating, or are each implemented using total internal reflection on the hypotenuse of the prism. In one aspect, an angle θ formed by the intersection of a plane including reflective surface 1041R and a plane including surface 1011R of image capture sensor 1010R_V and surface 1016R_HS of image capture sensor 1015R_HS is a forty-five degree angle and so the prism is referred to as a forty-five degree prism. Surface 1041R of a forty-five degree prism exhibits total internal reflection when the medium proximal to surface 1014R is air and so surface 1041R is a reflective surface.

Visible color image capture sensor 1010L_V and hyperspectral image capture sensor 1015L_HS are coplanar, i.e., top sensor surfaces 1011L_V and 1016L_HS are effectively in the same plane. Bottom surfaces of sensors 1010L_V and 1015L_HS are on a plane defined by a first surface of platform 1012. Similarly, visual image capture sensor 1010R_V and hyperspectral image capture sensor 1015R_HS are coplanar, e.g., top surfaces 1011R_V and 1016R_HS are effectively in the same plane. Bottom surfaces of sensors 1010R_V and 1015R_HS are on a plane defined by a second surface of platform 1012. Platform 1012 may be composed of two planar parts, e.g., two ceramic parts bonded along axis 1090. The first surface of platform 1012 is opposite and removed from the second surface of platform 1012.

In one aspect, a first semiconductor die 1017R including two image capture sensors 1010R_V, 1015R_HS is mounted on a first ceramic platform. A second semiconductor die 1017L including two image capture sensors 1010L_V, 1015L_HS is mounted on a second ceramic platform. The two ceramic platforms are then bonded together to form platform 1012. Wires to the two dies 1017R, 1017L are passed through a channel or channels in platform 1012. The use of two image capture sensors in a die is illustrative only and is not intended to be limiting. In some aspects, the two image sensors are in separate dies. (see FIG. 8A).

In some aspects, platform 1012 may not be used and the two sets of image capture sensors are included in a single structure configured to provide the necessary connections to power, control, and video cables. Also, the use of the two coplanar image capture sensors in an image capture unit as shown in FIG. 9 is only illustrative and is not intended to be limiting.

The coplanar configuration of the image capture sensors eliminates the need for calibration to compensate for lens artifacts and re-registration of different images captured by image captures sensors 1010R_V/1015R_HS (first pair) and 1010L_V/1015L_HS (second pair). As described above, the spatial relation between the two image capture sensors within a given pair is constant, and since the image captures sensors within a given pair share a common lens assembly, i.e., a common front end optical structure, spatial registration of a pair of images captured by the two image capture sensors remains constant over time and during changing optical conditions, such as changing focus. In a monoscopic endoscope, only one of image capture units 1020L, 1020R is used.

Visible color image capture sensors 1010R_V and 1010L_V are each equivalent to visible color image capture sensor 921_V. Therefore, the aspects described above with respect to visible color image capture sensor 921_V are not repeated here.

Filter assemblies 1050L and 1050R are each equivalent to filter assembly 940. Therefore, the aspects described above with respect to registration assistance filter assembly 940 and with respect to filters 941 and 942 are not repeated here.

Image Capture Unit for Time Sequential Illumination

Figure 10A:
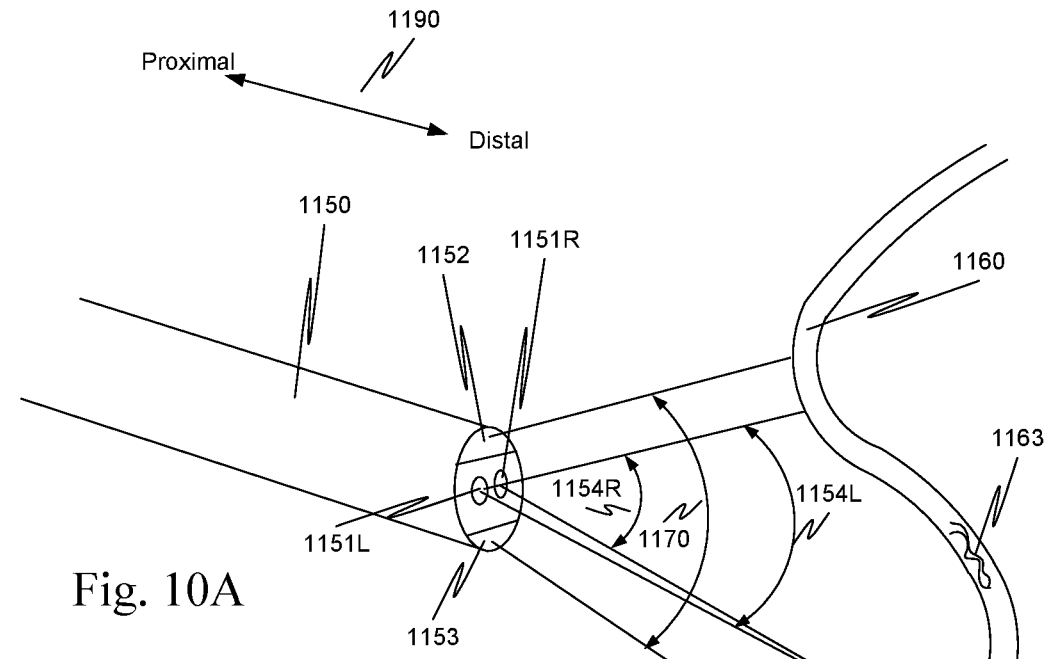
FIG. 10A is an illustration of a surgical device that includes one of the cameras of FIG. 8A, 9, or 10B.

FIG. 10A is an illustration of yet another endoscope 1150 that includes a novel image capture unit that simultaneously captures a visible frame and a hyperspectral frame. Endoscope 1150 is one example of endoscope 101.

In one aspect, endoscope 1150 is used with a combination of white light illumination and time sequential hyperspectral illumination. In this example, endoscope 1150 is a stereoscopic endoscope, but in another aspect endoscope 1150 is a monoscopic endoscope. The image capture unit or image capture units can be located within the distal end of endoscope 1150, or can be located outside the body of endoscope 1150 at the proximal end of endoscope 1150. Arrow 1190 defines the distal and proximal directions.

In aspect, the distal end of endoscope 1150 includes two light pipe guide areas 1152, 1153 that provide, in one aspect, a cone 1170 of white light illumination or a combination of white light illumination and hyperspectral illumination on tissue 1160. A feature 1163 of tissue 1160 is more salient when illuminated with hyperspectral illumination, e.g., near-infrared illumination.

The distal end of endoscope 1150 also includes, in this aspect, a first image capture unit window 1151L and a second image capture unit window 1151R. A first image capture unit coupled to image capture unit window 1151L has a first field of view 1154L. A second image capture unit coupled to image capture unit window 1151R has a second field of view 1154R.

Figure 10B:
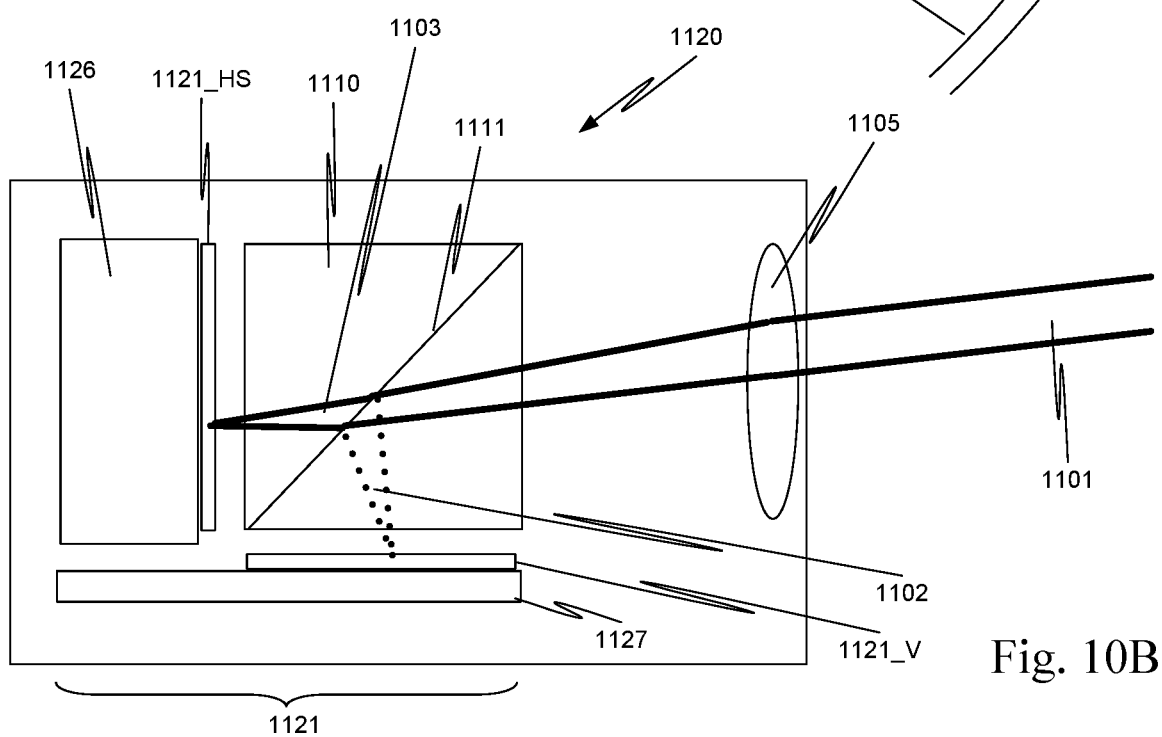
FIG. 10B is a diagram of a camera used with time sequential hyperspectral illumination, which simultaneously captures a visible frame and a hyperspectral frame.

FIG. 10B is an illustration of one aspect of an image capture unit 1120 suitable for use as cameras 220L and 220R with a time sequential hyperspectral illumination source and a white light illumination source. Light from one or more illumination channels in endoscope 1150 illuminates tissue 1160 in this example. While it not shown in FIG. 10B, one or more surgical instruments within the field of view of endoscope 1150 may also be illuminated via light from the illumination channel. The use of an illumination channel in an endoscope is illustrative only and is not intended to be limiting in the various examples presented in this description. The illumination may be provided by an illumination source in the endoscope or by some other apparatus that is internal or external to the endoscope.

Light reflected from tissue 1160 and any fluorescence are received by lens assembly 1105 as light 1101. Lens assembly 1105 may include one of more optical components that direct the received light to sensor assembly 1121. In some aspects, lens assembly 1105 is folded.

Light from lens assembly 1105 passes to sensor assembly 1121. In some aspects, lens assembly 1105 exploits the different back focal lengths afforded by the mechanical separation of image sensors 1121_V and 1121_HS and the longitudinal chromatic aberration is accommodated for by positioning the sensors at different distances from surface 1111

Within sensor assembly 1121, the light interacts with a beam splitter 1111 arranged on the diagonal of a beam splitter cube 1110 in this aspect. In one aspect, beam splitter 1111 is implemented as a buried coated surface.

The use of a beam splitter cube is illustrative only and is not intended to be limiting. For example, beam splitter 1111 could be a filter positioned in space.

Beam splitter 1111 directs a first portion 1102 of light received from lens assembly 1105 to visible color image capture sensor 1121_V and directs a second portion 1103 of light received from lens assembly 1105 to hyperspectral image capture sensor 1121_HS. In the example of FIG. 10B, beam splitter 1111 reflects first portion 1102 of the light received from lens assembly 1105 to visible color image capture sensor 1121_V and transmits the second portion 1103 of light received from lens assembly 1105 to hyperspectral image capture sensor 1121_HS. In each of the aspects described herein, the light is directed onto, i.e., is focused on, a surface of an image capture sensor and so for brevity it is said that the light is directed onto the image capture sensor.

The wavelengths of light in first portion 1102 of light and in second portion 1103 of light are determined by the characteristics of beam splitter 1111. In one example, beam splitter 1111 is configured so that first portion 1102 of light is a first portion of visible light received from lens assembly 1105, and second portion 1103 of light is a combination of a second portion of the visible light received from lens assembly 1105 and hyperspectral light received from lens assembly 1105. In one example, first portion 1102 is visible light in the visible spectrum with wavelengths about 670 nm and smaller, and second portion 1103 of light 1101 is visible light with wavelength larger than 670 nanometers, and hyperspectral light received from lens assembly 1105, e.g., light with wavelengths longer than about 670 nanometers and smaller than or equal to 1.7 micrometers. Here, about 670 nanometers is used because when beam splitter 1111 is implemented as a buried coated layer, the coated layer has a transition zone where some portion of the incident light is directed to both image capture sensors. For example, light with wavelengths of 670 nm±20 nm transitions from going to visible color image capture sensor 1121_V to hyperspectral image capture 1121_HS. Hence, about 670 nanometers means within the transition zone about 670 nanometers.

The first portion 1102 of light 1101 is focused on visible color image capture sensor 1121_V. In one aspect, visible color image capture sensor 1121_V captures light having wavelengths in the range of 400 nanometers to about 670 nanometers. For example, visible color image capture sensor 1121_V is a small pixel CMOS image capture sensor with a Bayer red-green-blue color filter array or a red-green-blue-white color filter array. Visible color image capture sensor 1121_V, sometimes referred to as sensor 1121_V, is coupled to mechanicals and electronics 1127. Mechanicals and electronics 1127 include mechanicals for holding sensor 1121_V and electronics connected to sensor 1121_V.

Second portion 1103 of light 1101 from lens assembly 1105 is focused on hyperspectral image capture sensor 1121_HS. In one aspect, hyperspectral image capture sensor 1121_HS captures light having wavelengths in the range of about 670 nanometers to 1.7 micrometers. Hyperspectral image capture sensor 1121_HS is a monochrome large pixel image capture sensor, e.g., an InGsAs sensor with 5 to 20 micrometer pixels or an HgCdTe sensor with similarly sized pixels.

Hyperspectral image capture sensor 1121_HS and visible color image capture sensor 1121_V can be implemented with different semiconductor technologies and as such may have different shutter architectures, e.g., a rolling shutter for visible color image capture sensor 1121_V and a global shutter for hyperspectral image capture sensor 1121_HS. The positioning of the two image sensors permits independent focusing at the time of manufacture. Additionally, the two image sensors may have different pixel sizes as well as different active areas.

Hyperspectral image capture sensor 1121_HS, sometimes referred to as sensor 1121_HS, is coupled to mechanicals, cooling, and electronics 1126. Mechanicals, cooling, and electronics 1126 include mechanicals for holding sensor 1121_HS, cooling for sensor 1121_HS, and electronics connected to sensor 1121_HS.

Image capture unit 1120 can also be implemented as shown in FIG. 9. However, for time sequential hyperspectral illumination, registration assistance filter assemblies 1050L and 1050R are removed.

In one aspect, instead of monochrome hyperspectral image capture sensor 1121_HS, a color filter array over pixels of sensor 1121_HS generate another set of "primaries," which are the combination of the instantaneous illumination spectral content and the filters over the pixels. This reduces the number of sequential illumination patterns because the illumination can simultaneously include light which will illuminate the pixels behind each filter. This is beneficial as it reduces the time for acquisition, and simplifies the process as it removes the temporal artifacts associated with time sequential imaging. Thus, this approach obviates the need for tissue tracking and re-aligning the images because an image from the hyperspectral imager contains the information for all the wavebands simultaneously. The trade-off is a reduction in spatial resolution.

Lens assembly 1105 may contain a filter to block some wavelength of light which is used for exciting a fluorophore in the tissue—for example, if the fluorescence and excitation are in the near infra-red portion of the spectrum, this may be done without compromising the image quality of the visible image. In that case, the illuminator may use the excitation light as one of the time sequential wavebands, and the fluorophore signal will be 'seen' by the camera and not overwhelmed by the excitation because of the blocking filter in lens assembly 1105. The fluorophore may be a naturally occurring molecule or a molecule introduced into the tissue in order to tag a particular tissue type, condition, or other element of clinical interest. One can thus intersperse the detection of a fluorophore with spectral imaging.

An Endoscope and a Second Tool with Hyperspectal Capability

Figure 11A:
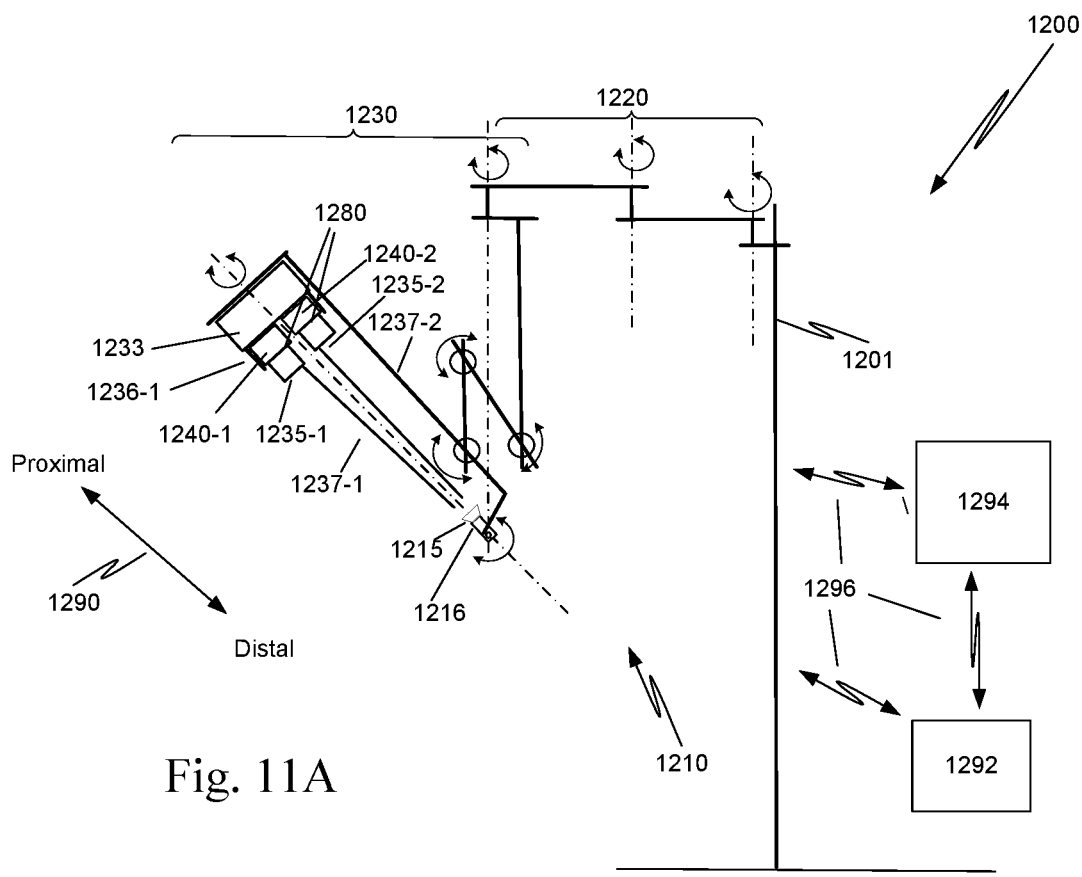
FIG. 11A is an illustration of another computer-assisted surgical system that uses the surgical devices described herein.

In the above example, an endoscope—monoscopic or stereoscopic—was attached in one aspect, to an arm of a computer-assisted surgical system and other surgical instruments were attached to a different arm of the computer-assisted surgical system. See FIG. 1. In another aspect, a single entry port is used. FIG. 11A is a schematic side view that illustrates aspects of a surgical system 1200 that includes an endoscopic imaging system 1292, a surgeon's console 1294 (master), and a patient side support system 1210 (slave), all interconnected by wired (electrical or optical) or wireless connections 1296. One or more electronic data processors may be variously located in these main components to provide system functionality. Examples are disclosed in U.S. patent application Ser. No. 11/762,165, which is incorporated by reference herein.

Patient side support system 1210 includes an entry guide manipulator. At least one surgical device assembly is coupled to the entry guide manipulator. Each surgical device assembly includes either a surgical instrument or a camera instrument. For example, in FIG. 11A, one surgical device assembly includes an instrument 1235-1 with a shaft 1237-1 that extends through entry guide 1215 during a surgical procedure. Typically, entry guide 1215 includes a plurality of channels.

Imaging system 1292 performs image processing functions on, e.g., captured endoscopic imaging data of the surgical site and/or preoperative or real time image data from other imaging systems external to the patient, as described herein. Imaging system 1292 outputs processed image data (e.g., images of the surgical site, as well as relevant control and patient information) to a surgeon at surgeon's console 1294. In some aspects, the processed image data is output to an optional external monitor visible to other operating room personnel or to one or more locations remote from the operating room (e.g., a surgeon at another location may monitor the video; live feed video may be used for training; etc.).

Surgeon's console 1294 includes multiple degrees-of-freedom ("DOF") mechanical input devices ("masters") that allow the surgeon to manipulate the instruments, entry guide(s), and imaging system devices, which are collectively referred to as slaves. These input devices may in some aspects provide haptic feedback from the instruments and surgical device assembly components to the surgeon. Console 1294 also includes a stereoscopic video output display positioned such that images on the display are generally focused at a distance that corresponds to the surgeon's hands working behind/below the display screen. These aspects are discussed more fully in U.S. Pat. No. 6,671,581, which is incorporated by reference herein.

Control during insertion of the instruments may be accomplished, for example, by the surgeon moving the instruments presented in the image with one or both of the masters; the surgeon uses the masters to move the instrument in the image side to side and to pull the instrument towards the surgeon. The motion of the masters commands the imaging system and an associated surgical device assembly to steer towards a fixed center point on the output display and to advance inside the patient.

In one aspect, the camera control is designed to give the impression that the masters are fixed to the image so that the image moves in the same direction that the master handles are moved. This design causes the masters to be in the correct location to control the instruments when the surgeon exits from camera control, and consequently this design avoids the need to clutch (disengage), move, and declutch (engage) the masters back into position prior to beginning or resuming instrument control.

In some aspects the master position may be made proportional to the insertion velocity to avoid using a large master workspace. Alternatively, the surgeon may clutch and declutch the masters to use a ratcheting action for insertion. In some aspects, insertion may be controlled manually (e.g., by hand operated wheels), and automated insertion (e.g., servomotor driven rollers) is then done when the distal end of the surgical device assembly is near the surgical site. Preoperative or real time image data (e.g., MRI, X-ray) of the patient's anatomical structures and spaces available for insertion trajectories may be used to assist insertion.

Patient side support system 1210 includes a floor-mounted base 1201, or alternately a ceiling mounted base (not shown). Base 1201 may be movable or fixed (e.g., to the floor, ceiling, wall, or other equipment such as an operating table).

Base 1201 supports an arm assembly that includes a passive, uncontrolled setup arm assembly 1220 and an actively controlled manipulator arm assembly 1230. The actively controlled manipulator arm assembly 1230 is referred to as entry guide manipulator 1230.

Cannula 1216 is removably coupled to a cannula mount. In this description, a cannula is typically used to prevent an instrument or an entry guide from rubbing on patient tissue. Cannulas may be used for both incisions and natural orifices. For situations in which an instrument or an entry guide does not frequently translate or rotate relative to its insertion (longitudinal) axis, a cannula may not be used. For situations that require insufflation, the cannula may include a seal to prevent excess insufflation gas leakage past the instrument or entry guide. Examples of cannula assemblies which support insufflation and procedures requiring insufflation gas at the surgical site may be found in U.S. patent application Ser. No. 12/705,439 (filed Feb. 12, 2010; disclosing "Entry Guide for Multiple Instruments in a Single Port System"), the full disclosure of which is incorporated by reference herein for all purposes. For thoracic surgery that does not require insufflation, the cannula seal may be omitted, and if instruments or entry guide insertion axis movement is minimal, then the cannula itself may be omitted. A rigid entry guide may function as a cannula in some configurations for instruments that are inserted relative to the entry guide. Cannulas and entry guides may be, e.g., steel or extruded plastic. Plastic, which is less expensive than steel, may be suitable for one-time use.

The various passive setup joints/links and active joints/links allow positioning of instrument manipulators to move the instruments and camera assembly with a large range of motion when a patient is placed in various positions on a movable table. In some embodiments, a cannula mount may be coupled to the first manipulator link.

Certain setup and active joints and links in the manipulator arm may be omitted to reduce the surgical system's size and shape, or joints and links may be added to increase degrees of freedom. It should be understood that the manipulator arm may include various combinations of links, passive joints, and active joints (redundant DOFs may be provided) to achieve a necessary range of poses for surgery. Furthermore, various instruments alone or surgical device assemblies including entry guides, multiple instruments, and/or multiple entry guides, and instruments coupled to instrument manipulators (e.g., actuator assemblies) via various configurations (e.g., on a proximal face or a distal face of the instrument transmission means or the instrument manipulator), are applicable in aspects of the present disclosure.

Each of plurality of surgical device assemblies 1280 includes an instrument manipulator assembly and one of a surgical instrument and a camera assembly. In FIG. 11A, two of a plurality of surgical device assemblies 1280 are visible, and each of the two visible surgical device assemblies includes an instrument manipulator assembly and a surgical instrument or a camera assembly. Each of instrument manipulator assemblies 1240-1 and 1240-2 is computer-assisted, in one aspect, and so each is sometimes referred to as a computer-assisted instrument manipulator assembly. Each of instrument manipulator assemblies 1240-1, 1240-2 is coupled to entry guide manipulator assembly 1233 by a different insertion assembly, e.g. instrument manipulator assembly 1240-1 is coupled to entry guide manipulator assembly 1233 by insertion assembly 1236-1.

In one aspect, insertion assembly 1236-1 is a telescoping assembly that moves the corresponding surgical device assembly away from and towards entry guide manipulator assembly 1233. In FIG. 11A, insertion assembly 1236-1 is in the fully retracted position.

Each instrument manipulator assembly 1240-1, 1240-2 includes a plurality of motors that drive a plurality of outputs in an output interface of instrument manipulator assembly 1240-1, 1240-2. Each of instruments 1235-1, 1235-2 includes a body that houses a transmission unit. The transmission unit includes an input interface including a plurality of inputs. Each of instruments 1235-1, 1235-2 also includes a shaft 1237-1, 1237-2 sometimes referred to as a main tube that extends in the distal direction from the body. An end effector is coupled to a distal end of the shaft of a surgical instrument, and an image capture unit, e.g., a camera, is included in a distal end of the shaft of a camera instrument, sometimes called an endoscope. See U.S. Patent Application No. 61/866,115 (filed on 15 Aug. 2013), which is incorporated by reference, for one example of an instrument manipulator assembly and a surgical instrument.

Each of instruments 1235-1, 1235-2 is coupled to the instrument mount interface of a corresponding instrument manipulator assembly 1240-1, 1240-2 so that a plurality of inputs in an input interface of the transmission unit in instrument 1235-1, 1235-2 is driven by plurality of outputs in the instrument mount interface of instrument manipulator assembly 1240-1, 1240-2. See U.S. Patent Application No. 61/866,115 (filed on 15 Aug. 2013).

In one aspect, one or more instrument manipulator assemblies may be configured to support and actuate a particular type of instrument, such as a camera instrument. As shown in FIG. 11A, the shafts of plurality of surgical device assemblies 1280 extend distally from a body of the instruments. The shafts extend through a common cannula 1216 placed at the entry port into the patient (e.g., through the body wall or at a natural orifice). In one aspect, an entry guide 1215 is positioned within cannula 1216, and each instrument shaft extends through a channel in entry guide 1215, so as to provide additional support for the instrument shafts.

The surgeries that can be performed using surgical system 1200 may be performed on different regions of the body. For example, one surgery may be performed through the mouth of a patient. Another surgery may be performed between the ribs of the patient. Other surgeries may be performed through other orifices of the patient or through an incision in the patient. Each different entry into a patient may require a different shape and/or different size of an entry guide. Thus, an appropriate entry guide 1215 is selected for a particular surgery.

In the aspect described above, an endoscope included or was coupled to an image capture unit that simultaneously captured a visible frame and a hyperspectral frame. However, in another aspect, a standard camera instrument 1235-2, e.g., a stereoscopic endoscope, is used in conjunction with a second tool, e.g., surgical instrument 1235-1, which includes a hyperspectral image capture unit and a depth measuring device, e.g., a depth camera, a ultrasound device, etc.

Figure 11B:
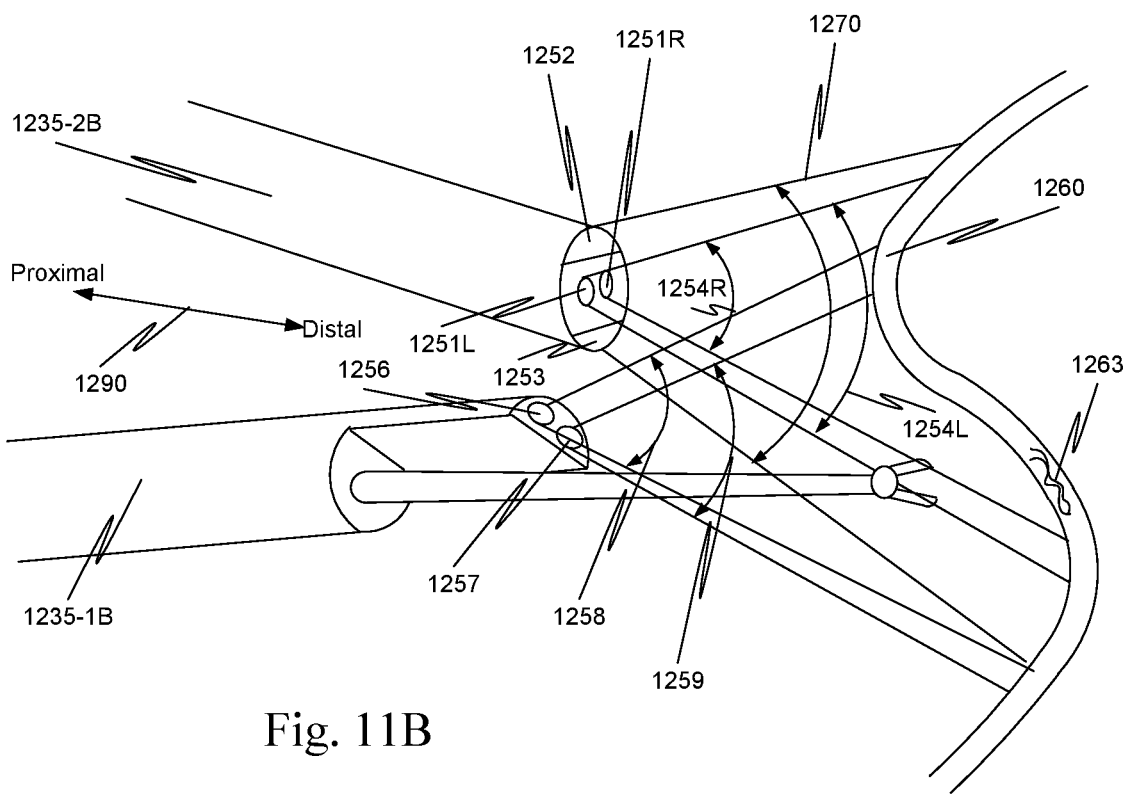
FIG. 11B is a more detail illustrated of two surgical devices used in the computer-assisted surgical system of FIG. 1 or in the computer-assisted surgical system of FIG. 11A.

FIG. 11B is a more detailed illustration of an endoscope 1235-2B and another surgical instrument 1235-1B. Surgical instrument 1235-1B has hyperspectral image capture capabilities.

In one aspect, endoscope 1235-2B is used with a combination of white light illumination and either time constant or time sequential hyperspectral illumination. In this example, endoscope 1235-2B is a stereoscopic endoscope, but in another aspect endoscope 1235-2B is a monoscopic endoscope. The image capture unit or image capture units can be located within the distal end of endoscope 1235-2B, or can be located outside the body of endoscope at the proximal end of endoscope 1235-2B. Arrow 1290 defines the distal and proximal directions.

In this aspect, the distal end of endoscope 1235-2B includes two light pipe guide areas 1252, 1253 that provide, in one aspect, a cone 1270 of white light illumination or a combination of white light illumination and hyperspectral illumination on tissue 1260. A feature 1263 of tissue 1260 is more salient when illuminated with hyperspectral illumination, e.g., near-infrared illumination.

The distal end of endoscope 1235-2B also includes, in this aspect, a first image capture unit window 1251L and a second visible image capture unit window 1251R. A first visible image capture unit coupled to image capture unit window 1251L has a first field of view 1254L. A second visible image capture unit coupled to image capture unit window 1251R has a second field of view 1254R. The frames captured by the visible image capture unit are processed as described above for visible image processing pipeline 310 to produce a video sequence of stereoscopic visible images on surgeon's console 1294.

The distal end of surgical instrument 1235-1B also includes, in this aspect, a hyperspectral image capture unit window 1256 and a depth sensing unit window 1257. A hyperspectral image capture unit coupled to hyperspectral image capture unit window 1256 has a third field of view 1258. A depth sensing unit coupled to depth sensing window 1257 has a fourth field of view 1259.

As shown in FIG. 11B, which is not to scale, the field of view of stereoscopic endoscope 1235-2B overlaps with field of view 1258 of the hyperspectral image capture unit and field of view 1259. Each of the fields of view includes feature 1263 of tissue 1260.

Figure 12A:
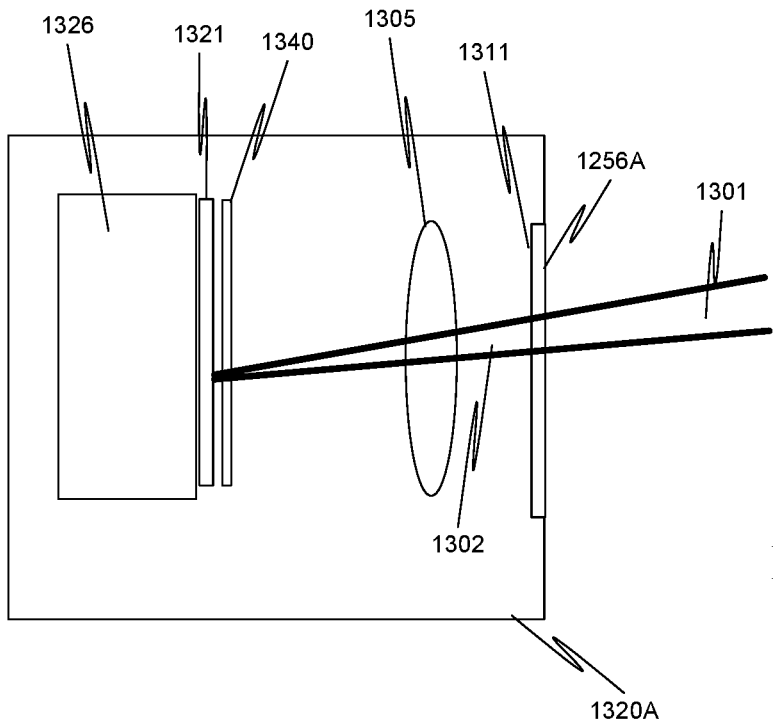
FIG. 12A is a diagram of a camera used with time constant hyperspectral illumination in the first surgical instrument of FIG. 11A.
Figure 12B:
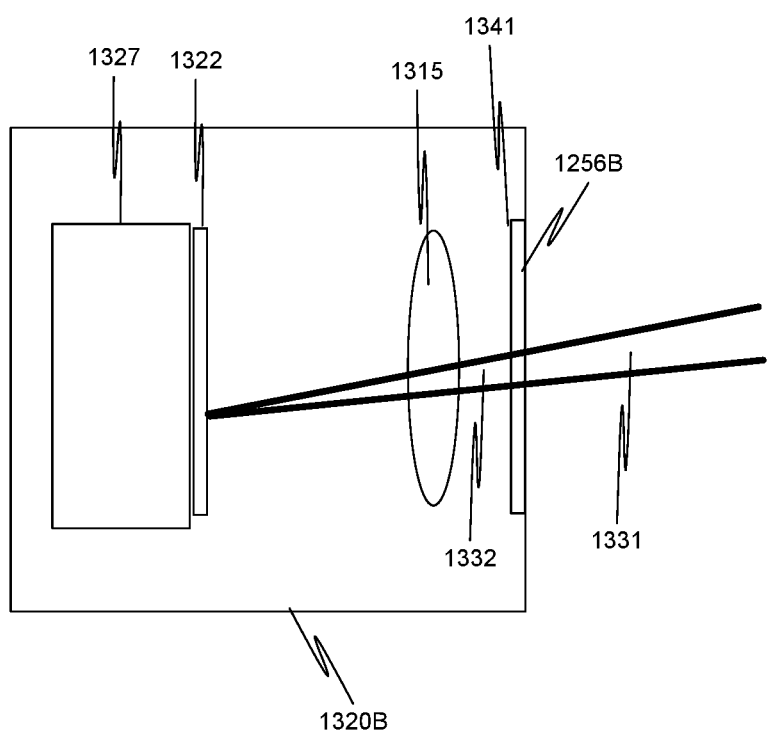
FIG. 12B is a diagram of a camera used with time sequential hyperspectral illumination in the first surgical instrument of FIG. 11A.

FIGS. 12A and 12B are examples of hyperspectral cameras suitable for use in surgical instrument 1235-1B. In the example of FIG. 12A, hyperspectral image capture unit 1320A is used in surgical instrument 1235-1B for a time constant hyperspectral illumination source.

Hyperspectral image capture unit 1320A includes window 1256A in the distal end of the surgical instrument. Window 1256A includes a coating 1311 that passes wavelengths of interest, e.g., 700 nanometers to 2.4 micrometers wavelengths. Thus, light 1301, which is light reflected from tissue 1260 and any fluorescence from tissue 1260, is received by window 1256A. Lens assembly 1305 of hyperspectral image capture unit 1320A receives light 1302 that is passed though coating 1311 on window 1256A. In another aspect, a filter is placed between window 1256A and lens assembly 1305 instead of using the coating on window 1256A. Filter 1311 is configured to pass a combination of a portion of the visible light received from tissue 1260 and hyperspectral light received from tissue 1260.

Lens assembly 1305 may include one of more optical components that direct, i.e., focus, the received light to sensor assembly 1321. In some aspects, lens assembly 1305 is folded.

The combination of the visible light received from lens assembly 1305 and hyperspectral light received from lens assembly 1305 is focused on hyperspectral image capture sensor 1321. In one aspect, hyperspectral image capture sensor 1321 captures light having wavelengths in the range of 700 nanometers to 1.7 or 2.4 micrometers. The range of wavelengths captured by each pixel of image capture sensor 1324 is dependent on the characteristics of filter assembly 1340 and the spectral response of sensor 1321. Filter assembly 1340 is equivalent to filter assembly 940 described above, and so that description is not repeated here. Hyperspectral image capture sensor 1321 is a monochrome large pixel image capture sensor, e.g., an InGsAs sensor with 5 to 20 micrometer pixels or an HgCdTe sensor with similarly sized pixels. Hyperspectral image capture unit 1320 can have either a global shutter or a rolling shutter.

Hyperspectral image capture sensor 1321 sometimes referred to as sensor 1321, is coupled to mechanicals, cooling, and electronics 1326. Mechanicals, cooling, and electronics 1326 include mechanicals for holding sensor 1321, cooling for sensor 1321, and electronics connected to sensor 1321.

For systems with constant hyperspectral illumination, one or more wavebands are illuminating the scene and filter assembly 1340 adjacent to image capture sensor 1321 is pixelated to provide an image which encodes the hyperspectral information into a single frame.

FIG. 12B is an illustration of one aspect of an image capture unit 1320B suitable for use in surgical instrument 1235-1B with a time sequential hyperspectral illumination source and a white light illumination source. Hyperspectral image capture unit 1320B includes window 1256B in the distal end of the surgical instrument. Window 1256B includes a coating that passes wavelengths of interest, e.g., wavelengths longer than about 670 nanometers and shorter than or equal to 1.7 micrometers. Thus, light 1331, which is light reflected from tissue 1260 and any fluorescence, is received by window 1256B. Lens assembly 1315 of hyperspectral image capture unit 1320B receives light 1332 that is passed through the coating on window 1256B. In another aspect, a filter 1341 is placed between window 1256B and lens assembly 1315 instead of using the coating on window 1256B, or the coating is included in lens assembly 1315. Filter 1341 is configured to pass combination of a portion of the visible light received from tissue 1260 and hyperspectral light received from tissue 1260.

Lens assembly 1315 may include one of more optical components that direct the received light to sensor assembly 1322. In some aspects, lens assembly 1315 is folded with a fold prism before the image sensor.

Light from lens assembly 1315 passes to hyperspectral image capture sensor 1322, e.g., is focused on hyperspectral image capture sensor 1322. In one aspect, hyperspectral image capture sensor 1322 captures light having wavelengths in the range of 670 nanometers to 1.7 micrometers. Hyperspectral image capture sensor 1322 is a monochrome large pixel image capture sensor, e.g., an InGsAs sensor with 5 to 20 micrometer pixels or an HgCdTe sensor with similarly sized pixels.

Hyperspectral image capture sensor 1322, sometimes referred to as sensor 1322, is coupled to mechanicals, cooling, and electronics 1327. Mechanicals, cooling, and electronics 1327 include mechanicals for holding sensor 1322, cooling for sensor 1322, and electronics connected to sensor 1322.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the inventive aspects.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups.

All examples and illustrative references are non-limiting and should not be used to limit the claims to specific implementations and embodiments described herein and their equivalents. Any headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

While the memory is illustrated as a unified structure, this should not be interpreted as requiring that all memory is at the same physical location. All or part of the memory can be in a different physical location than a processor. Memory refers to a volatile memory, a non-volatile memory, or any combination of the two.

A processor is coupled to a memory containing instructions executed by the processor. This could be accomplished within a computer system, or alternatively via a connection to another computer via modems and analog lines, or digital interfaces and a digital carrier line.

Herein, a computer program product comprises a medium configured to store computer readable code needed for any one or any combination of the methods and/or processes described herein, or in which computer readable code for any one or any for any one or any combination of the methods and/or processes described herein is stored. Some examples of computer program products are CD-ROM discs. DVD discs, flash memory, ROM cards, floppy discs, magnetic tapes, computer hard drives, servers on a network and signals transmitted over a network representing computer readable program code. A tangible computer program product comprises a medium configured to store computer readable instructions for any one or any combination of the methods and/or processes described herein, or in which computer readable instructions for any one or any combination of the methods and/or processes described herein, is stored. Tangible computer program products are CD-ROM discs, DVD discs, flash memory, ROM cards, floppy discs, magnetic tapes, computer hard drives and other physical storage mediums.

In view of this disclosure, instructions for any one or any combination of the methods and/or processes described herein can be implemented in a wide variety of computer system configurations using an operating system and computer programming language of interest to the user.

What is claimed is:

1. A surgical system comprising:
   an illuminator comprising a white light illumination source and a hyperspectral illumination source;
   a camera having a sensor assembly, the sensor assembly comprising a first image capture sensor and a second image capture sensor, the first image capture sensor configured to capture a sequence of visible color frames and the second image capture sensor configured to capture a sequence of hyperspectral frames; and a controller configured to create a composite hyperspectral frame from a plurality of hyperspectral frames in the sequence of hyperspectral frames, the plurality of hyperspectral frames captured from a plurality of different camera locations and at a same waveband of hyperspectral light, and associate the composite hyperspectral frame with a visible color frame in the sequence of visible color frames.

2. The surgical system of claim 1, further comprising:
a robotic arm, the camera mounted on the robotic arm;
wherein the controller is configured to command the robotic arm to move the camera to each of the plurality of different camera locations and to command the camera to capture a hyperspectral frame at each of the plurality of different camera locations to form the plurality of hyperspectral frames.

3. The surgical system of claim 2, wherein the same waveband of hyperspectral light is output by the hyperspectral illumination source when the camera captures the hyperspectral frame at each of the plurality of different camera locations.

4. The surgical system of claim 1,
wherein the visible color frame includes a visible scene of a surgical site, and the composite frame includes a feature of the surgical site that is not visible in the visible scene.

5. The surgical system of claim 4, further comprising:
a display coupled to the controller to receive the composite frame and the visible color frame, the display displaying the feature superimposed with the visible scene.

6. The surgical system of claim 4, further comprising:
a display coupled to the controller and configured to receive the composite frame and the visible color frame, the display configured to display the feature superimposed with the visible scene in a picture within a picture.

7. The surgical system of claim 1, the camera further comprising:
a lens assembly common to the first image capture sensor and the second image capture sensor.

8. The surgical system of claim 7, the camera further comprising:
a beam splitter positioned between the lens assembly and the first and second image capture sensors.

9. The surgical system of claim 8, the camera further comprising:
a filter assembly positioned between the beam splitter and the second image capture sensor.

10. The surgical system of claim 1, the camera further comprising:
a filter assembly positioned to filter light focused on the second image capture sensor.

11. The surgical system of claim 10, the filter assembly comprising a striped filter.

12. The surgical system of claim 10, the filter assembly comprising a filter linearly variable with wavelength in one dimension.

13. The surgical system of claim 1, further comprising:
an endoscope including the illuminator and the camera.

14. The surgical system of claim 1, further comprising:
an endoscope mounted on a first manipulator, the endoscope including the camera; and
a surgical device mounted on a second manipulator, the surgical device including the illuminator.

15. A surgical system comprising:
a camera; wherein the camera comprises: a sensor assembly comprising a first image capture sensor and a second image capture sensor, the first image sensor configured to capture the visible color frame, the second image sensor configured to capture the plurality of hyperspectral frames; and a lens assembly common to the first image capture sensor and the second image capture sensor; and
a controller configured to command the camera to capture a visible color frame and a plurality of hyperspectral frames, the plurality of hyperspectral frames captured from a plurality of different camera locations and at a same waveband, the controller further configured to create a composite hyperspectral frame from the plurality of hyperspectral frames and to associate the composite hyperspectral frame with the visible color frame.

16. The surgical system of claim 15, the camera further comprising:
a beam splitter positioned between the lens assembly and the first and second image capture sensors.

17. The surgical system of claim 15, the camera further comprising:
a filter assembly positioned to filter light focused on the second image capture sensor, the filter assembly comprising a striped filter or a filter linearly variable with wavelength in one dimension.

18. A method comprising:
capturing a sequence of visible color images by a first image capture unit of a surgical system;
capturing a plurality of hyperspectral images from a plurality of different camera locations and at a same waveband by a second image capture unit of the surgical system;
processing the plurality of hyperspectral images to obtain a composite hyperspectral image; and
associating the composite hyperspectral image with a visible color frame in the sequence of visible color images.

19. A surgical system comprising:
an illuminator comprising a white light illumination source and a hyperspectral illumination source;
a camera having a sensor assembly, the sensor assembly comprising a first image capture sensor and a second image capture sensor, the first image capture sensor configured to capture a sequence of visible color frames and the second image capture sensor configured to capture a sequence of hyperspectral frames; and
a controller configured to create a composite hyperspectral frame from a plurality of hyperspectral frames in the sequence of hyperspectral frames, the plurality of hyperspectral frames captured from a plurality of different camera locations and at a same waveband of hyperspectral light, and associate the composite hyperspectral frame with a visible color frame in the sequence of visible color frames, wherein the composite hyperspectral frame has a resolution that is higher than a resolution of each hyperspectral frame in the plurality of hyperspectral frames.

* * * * *